(12) United States Patent
Johnson

(10) Patent No.: US 7,620,531 B1
(45) Date of Patent: Nov. 17, 2009

(54) METHOD FOR DETERMINING AND REPRESENTING FOOD PRODUCTS BASED ON NUTRIENT DENSITY RATING AND PREDICTED SATIATING EFFECT

(75) Inventor: Ronald B. Johnson, Casa Grande, AZ (US)

(73) Assignee: CondeNet, Inc., New York, NY (US)

( * ) Notice: Subject to any disclaimer, the term of this patent is extended or adjusted under 35 U.S.C. 154(b) by 221 days.

(21) Appl. No.: 11/302,080

(22) Filed: Dec. 12, 2005

(51) Int. Cl.
  *G06F 17/10* (2006.01)
  *G09B 19/00* (2006.01)
  *G01N 33/02* (2006.01)
(52) U.S. Cl. .......................... 703/2; 434/127; 426/231; 702/19; 708/133
(58) Field of Classification Search ............... None
  See application file for complete search history.

(56) References Cited

U.S. PATENT DOCUMENTS

| 4,321,674 | A | 3/1982 | Krames et al. |
| 5,412,560 | A | 5/1995 | Dennison |
| 6,040,531 | A | 3/2000 | Miller-Kovach et al. |
| 2003/0208113 | A1* | 11/2003 | Mault et al. ............ 600/316 |
| 2005/0008994 | A1 | 1/2005 | Bisogno |
| 2005/0025864 | A1 | 2/2005 | Gordon |

OTHER PUBLICATIONS

NutritionData.com (website [online]. Available on Nov. 26, 2004 on NutritionData.com. Retrieved from the internet archive on Feb. 26, 2007 using the Internet: <URL:web.archive.org/web/20041126135937/http://www.nutritiondat.com/better-choices-diet.html).*
NutritionData.com (website [online]. Available on Nov. 26, 2004 on NutritionData.com. Retrieved from the internet archive on Feb. 26, 2007 using the Internet: <URL:web.archive.org/web/20041126232823/http://www.nutritiondat.com/Fullness-actor.html>).*
NutritionData.com (website [online]. Available on Nov. 26, 2004 on NutritionData.com. Retrieved from the internet archive on Feb. 26, 2007 using the Internet<URL:web.archive.org/web/20041107011207/http://www.nutritiondat.com/analysis-help.html>).*
Drewnowski (American journal of Clinical Nutrition, vol. 82, No. 4, p. 721-732, Oct. 2005).*
Holt et al. (European Journal of Clinical Nutrition, vol. 49, p. 675-690, 1995).*
Scheidt et al. (Journal of Nutrition Education and Behavior, vol. 36, No. 1, p. 35-39, Jan./Feb. 2004).*

* cited by examiner

*Primary Examiner*—Marjorie Moran
*Assistant Examiner*—Karlheinz R Skowronek
(74) *Attorney, Agent, or Firm*—Kramer Levin Naftalis & Frankel LLP

(57) ABSTRACT

A method of assisting individuals in making food choices by providing two nutritional indices. One is a numerical expression of a food's overall nutrient density and the other is a separate numerical expression that relates to a food's caloric density that is a prediction of the satiating effect of a food. A visual aid in the form of a graph or chart is provided so individuals using the indices can refer to the chart to determine food selections in accordance with the individual's dietary goals.

34 Claims, 7 Drawing Sheets

Sample label for
Eggplant, cooked with salt

Nutrition Facts

Serving Size 1 cup (99g)
Servings Per Container 1

Amount Per Serving

| Calories 35 | Calories from Fat 2 |
|---|---|

| | % Daily Value* |
|---|---|
| Total Fat 0g | 0% |
| Saturated Fat 0g | 0% |
| Trans Fat 0g | |
| Cholesterol 0mg | 0% |
| Sodium 237mg | 10% |
| Total Carbohydrate 9g | 3% |
| Dietary Fiber 2g | 10% |
| Sugars 3g | |
| Protein 1g | |

| Vitamin A | 1% | • | Vitamin C | 2% |
|---|---|---|---|---|
| Calcium | 1% | • | Iron | 1% |

*Percent Daily Values are based on a 2,000 calorie diet. Your daily values may be higher or lower depending on your calorie needs:

| | Calories | 2,000 | 2,500 |
|---|---|---|---|
| Total Fat | Less than | 65g | 80g |
| Sat Fat | Less than | 20g | 25g |
| Cholesterol | Less than | 300mg | 300mg |
| Sodium | Less than | 2,400mg | 2,400mg |
| Total Carbohydrate | | 300g | 375g |
| Fiber | | 25g | 30g |

Calories per gram:
Fat 9   •   Carbohydrate 4   •   Protein 4

Figure 1

Sample Fullness Factors

| Food | FF | |
|---|---|---|
| Bean sprouts | 4.6 | |
| Watermelon | 4.5 | |
| Grapefruit | 4.0 | |
| Carrots | 3.8 | |
| Oranges | 3.5 | |
| Fish, broiled | 3.4 | |
| Chicken breast, roasted | 3.3 | |
| Apples | 3.3 | |
| Sirloin steak, broiled | 3.2 | |
| Oatmeal | 3.0 | |
| Popcorn | 2.9 | ⇧ |
| Baked potato | 2.5 | |
| Lowfat yogurt | 2.5 | more filling |
| Banana | 2.5 | per Calorie |
| Macaroni and cheese | 2.5 | |
| Brown rice | 2.3 | less filling |
| Spaghetti | 2.2 | per Calorie |
| White rice | 2.1 | |
| Pizza | 2.1 | ⇩ |
| Peanuts | 2.0 | |
| Ice cream | 1.8 | |
| White bread | 1.8 | |
| Raisins | 1.6 | |
| Snickers® bar | 1.5 | |
| Honey | 1.4 | |
| Sugar (sucrose) | 1.3 | |
| Glucose | 1.3 | |
| Potato chips | 1.2 | |
| Butter | 0.5 | |

Figure 3

Sample Nutrient Density Ratings

| Food | NDR | |
|---|---|---|
| Bean sprouts | 4.8 | |
| Carrots | 4.3 | |
| Baked potato | 4.0 | |
| Oranges | 3.9 | |
| Watermelon | 3.8 | |
| Grapefruit | 3.6 | |
| Popcorn | 3.3 | |
| Oatmeal | 3.2 | |
| Spaghetti | 3.0 | |
| Brown rice | 2.9 | |
| Fish, broiled | 2.8 | ⇧ |
| Banana | 2.8 | |
| Apples | 2.7 | more nutrients |
| White bread | 2.6 | per Calorie |
| Peanuts | 2.5 | |
| Sirloin steak, broiled | 2.4 | less nutrients |
| Macaroni and cheese | 2.3 | per Calorie |
| Potato chips | 2.3 | ⇩ |
| Chicken breast, roasted | 2.2 | |
| White rice | 2.1 | |
| Raisins | 2.0 | |
| Lowfat yogurt | 1.6 | |
| Pizza | 1.5 | |
| Ice cream | 1.3 | |
| Snickers® bar | 1.2 | |
| Honey | 1.1 | |
| Sugar (sucrose) | 1.1 | |
| Glucose | 1.1 | |
| Butter | 0.8 | |

Figure 4

METHOD FOR DETERMINING AND REPRESENTING FOOD PRODUCTS BASED ON NUTRIENT DENSITY RATING AND PREDICTED SATIATING EFFECT

FIELD OF THE INVENTION

A method for selecting foods for improved health, hunger control, nutrition and weight control utilizing calculated ratings for nutrient density and satiating effect.

BACKGROUND OF THE INVENTION

Many individuals attempt to follow special diets as a result of health problems, to improve fitness and for weight loss. Most diets are generally based on specific recommendations from nutritional experts. Experts commonly recommend "good" foods and "bad" foods which are to be avoided or consumed in limited quantity. One problem with this type of system is that food lists are finite in nature, while the range of possible food selections is nearly unlimited. Tens of thousands of new food products are introduced to the market each year. Without an effective system for rating foods, dieters have no certain way of evaluating the suitability of available foods for their particular diet and nutritional goals. To overcome this deficiency, some systems have been developed that rate foods based on their nutrient content. These systems typically focus only on total calories or the amount of a single nutrient such as fat or carbohydrates in a food item. The systems lack effectiveness because they ignore dozens of additional nutrients that have a proven impact on health and diet.

Others have developed more complex food rating systems, but such systems generally only focus on a single goal such as weight loss. These systems are more complex and generally, because of their focused nature are ineffective for individuals who have other goals such as weight gain or maximizing health.

U.S. Pat. No. 6,040,531 entitled "Process for Controlling Body Weight" teaches a device independent calculation method for ranking foods. The method considers a limited number of nutrients and is dependent on food serving size. Further, the patent focuses only on weight loss and does not suggest any way of displaying rankings in a spatial orientation.

Another patent in this area, U.S. Pat. No. 5,412,560, teaches a dietary analysis method, but focuses only on the comparison and feedback of total nutrient consumption to government recommendations. Again, this patent does not teach methods of comparing individual foods.

Another system that is used as a meal-planning tool is called The Glycemic Index or GI. Basically the GI is a scale that ranks carbohydrate-rich foods based on the amount they raise blood glucose levels compared to glucose or white bread. Thus, the GI rates carbohydrate-rich foods according to the glycemic response. In general, low GI foods are preferred. GI is helpful in managing blood sugar but, again, focuses on a limited dietary aspect of nutrition.

BRIEF SUMMARY OF THE INVENTION

Briefly, the present invention relates to a method to enable individuals to select proper foods for improving health, controlling hunger and managing body weight based on calculations derived from a food's measured nutritional content.

The method involves assigning a ranking to food based on a combination of its calculated nutrient density (NDR), and predicted satiating affect which is termed the "Fullness Factor" (FF). The nutrient density represents a selectively weighted overall nutrient density of the food and is calculated by a formula that yields a numerical rating or scale that proportionately rewards foods that have the highest amount of nutrients per calorie for nutrients that the FDA deems essential.

The nutritional method of the invention further involves the calculation of a second factor (the "Fullness Factor" or FF) that represents an estimated satiating effect of food. The FF predicts the satiating effect of a food on a numeric scale. A high FF number indicates that the food will be more satisfying per calorie than a food with a low FF number.

The two calculating factors or indices FF and NDR may then be represented and interpreted in an easy to use manner such as on a visual format. One format is termed a "Nutritional Target Map" (NTM) which allows the user using the factors to determine appropriate foods consistent with the individuals nutritional goals such as weight loss, nutritional benefits and healthy weight gain.

The nutritional system of the present invention provides significant advantages and does not require a computer or any other device to enable the individual to make the necessary nutritional determinations and choices. Foods are ranked based on their suitability for multiple dietary goals, not a single objective such as weight loss alone. The system determines rankings based on the food's content of multiple nutrients and determines rankings independent of food serving size. The FF and NDR ratings may then be displayed in spatial orientation on a Nutritional Target Map which, in a preferred embodiment, plots FF and NDR on the coordinates of a graph. Other graphical representations may also be used to present or represent these factors.

BRIEF DESCRIPTION OF THE DRAWINGS

The above and other objects and advantages will be better understood and appreciated from the following drawings in which:

FIG. 1 is a representation of a typical Nutrition Facts label for eggplant;

FIG. 3 is a table displaying the Fullness Factor for a number of selected foods;

FIG. 4 is a table displaying the NDR for a number of foods;

DETAILED DESCRIPTION OF THE DRAWINGS

Nutritional Facts Label

Figure 2:
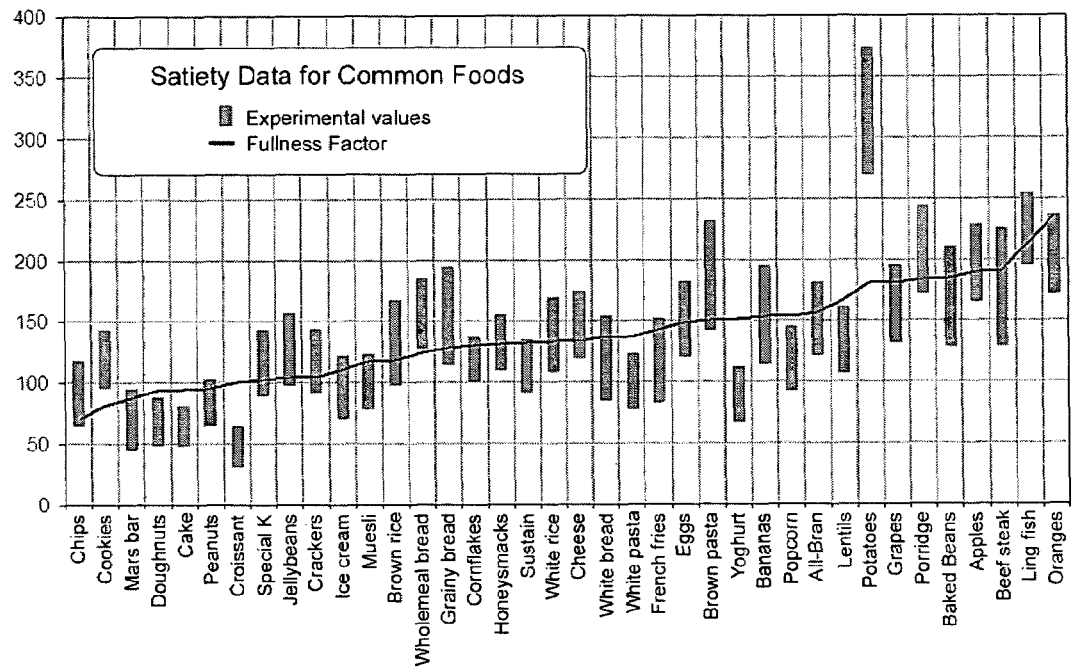
FIG. 2 is a graphical representation of the satiety data for some common foods.

Turning now to the drawings and more particular FIG. 1 represents a Nutritional Facts label for cooked eggplant. The information on the main top section of the sample Nutritional Facts label may vary with each food product, but contains specific product information such as serving size, calories and nutrient information. The bottom portion of the label contains a footnote with daily values (DV) for 2000 and 2500 calorie diets. The footnote provides recommended dietary information for some important nutrients including fats, sodium and fiber. The footnote is found primarily on larger packages and does not vary from product to product. Information on understanding and use of the nutritional facts label can be found at www.cfsan.fda.gov.

Various information appears on the label such as serving size as well as calories and calories from fat. Calories provide a measure of the energy an individual receives from a serving of food. The calorie section of the label will help an individual manage weight. In the example, there are 35 calories in one serving of cooked eggplant and 2 of the 35 calories come from fat. The nutrient section lists key nutrients that impact an individual's health. In general, consumption of nutrients such as fat, cholesterol and sodium should be limited by many individuals to avoid problems with chronic diseases like heart disease, some cancers and high blood pressure.

Many Americans do not consume enough dietary fiber, vitamins such as vitamins A and C, or minerals such as calcium and iron. The Nutrition Facts label provides guidance and not only helps limit certain nutrients, but helps the individual to increase other nutrients.

Following the dietary advise appearing at the footnote, an individual is given recommended guidelines to follow. The label further indicates a percent daily value of nutrients found in the labeled product based on serving sizes. For example, the sodium in one serving is listed on the sample Nutritional Facts label as 10% which is very helpful in determining consumption of the remaining allowance for a nutrient such as sodium. However, guidelines, such as shown on the label of FIG. 1, do not provide an estimate of the satiating affect of food. Nor does such labeling represent the nutritional benefit of the food, although it may serve as a guideline in this respect. The Nutrition Facts label requires substantial interpretation in order to provide a dietary guideline. Further, such labels do not provide a graphic guide in an easy to read and interpret manner. The present invention involves the calculation of a factor that represents an estimate of the satiated affect of food as well as the calculation of the factor that represents the nutritional benefit of the food. The factors may be calculated using the data appearing on a Nutrition Facts label as seen in FIG. 1.

The Fullness Factor

The satiating effect will first be discussed and is referred to as the "Fullness Factor" (FF). Hunger is one of the body's strongest and most beneficial stimuli. Hunger helps to insure that a person consumes sufficient calories for the individual's need. However, hunger is adverse to an individual trying to lose weight as the obvious way to reduce hunger is to consume food. Eating provides satiety, the pleasant feeling associated with the consumption of foods. However, certain foods are much better than others for satisfying hunger. A study such as the study of satiety index of common foods published by Holt in the *European Journal of Clinical Nutrition*, September 1995, indicates that satiety is most strongly related to the weight of foods consumed. Foods that weigh the most satisfy hunger the best, regardless of the number of calories contained. Higher quantities of certain nutrients in these foods such as protein and dietary fiber also appear to increase satiety. Caloric density alone is not a reliable predictor of satiety and excludes many enjoyable foods that individuals like to consume. As a result, a formula has been developed using a multivariate analysis of existing data to predict satiety from the nutrient content of a given food or recipe. The formula yields the satiety value which is the Fullness Factor (FF).

$$FF = \max(FFMIN, \min(FFMAX, C00 + C01 \cdot \max(CALMIN, CAL)^{E01} + C02 \cdot \min(PRMAX, PR)^{E02} + C03 \cdot \min(DFMAX, DF)^{E03} + C04 \cdot \min(TFMAX, TF)^{E04}))$$

where:

$\max(x,y)$ is a function that returns the maximum of either x or y, $\min(x,y)$ is a function that returns the minimum of either x or y, CAL is total Calories per 100 gram serving of the food, PR is grams of Protein per 100 grams, DF is grams Dietary Fiber per 100 g, and TF is grams total Fat per 100 g.

FFMIN, FFMAX, CALMIN, PRMAX, DFMAX, TFMAX, and C00 are constants, C01 through C04 are coefficients, and E01 through E04 are exponential powers. In the preferred embodiment, they have the following values:

FFMIN=0.5

FFMAX=5.0

CALMIN=30

PRMAX=30

DFMAX=12

TFMAX=50

C00=37/60

C01=2500/60

C02=3/60

C03=1/1620

C04=−1/138,000

E01=−0.7

E02=1.0

E03=3.0

E04=3.0

The calculation yields an FF with values that fall within the range of 0 to 5. Foods with high FF values are more likely to satisfy an individual's hunger with fewer calories. Foods with low FF values are less likely to satisfy hunger.

FIG. 2 is a graph showing predicted values against the experimental data taken from Holt's 1995 study. The graph shows a comparison of the Fullness Factor (FF) with existing satiety data. In the graph, each bar represents the range of reported satiety values from experimental foods and results vary somewhat from one participating individual to another. The solid line represents a calculated Fullness Factor. Fullness Factor approximates the predicted satiety responses with possible exception of potatoes. The Fullness Factor, when computed, will fall within the range of 0 to 5; however, the computed Fullness Factors were scaled to match the range reported in the Holt study. The food names shown are as reported in the study. To insure validity of all nutrient values, values were taken directly from the study which used foods primarily of Australian origin.

The Fullness Factor is calculated from the food's nutrient content using values from those nutrients that have been shown experimentally to have the greatest impact on satiety. There are other factors that can influence a food's ability to satisfy our hunger such as texture, taste and palatability. Palatability is a highly individual and subjective value that cannot be accurately measured. The Fullness Factor provides an estimate of food satiety prior to consumption.

The benefits of the Fullness Factor outweighs its limitations as satiating effect can now be accurately predicted solely from the nutrient content. This means that an individual can select foods and recipes that will be most supportive of the individual's diet. The Fullness Factor and the glycemic index discussed above are both non-dimensional ratings which are used to predict a body's response to particular foods. While the GI applies only to foods containing carbohydrates, the Fullness Factor can be used to evaluate all foods. FIG. 3 is a table which shows the Fullness Factor for a number of common foods. It should be noted that similarly designated foods may have substantially varying Fullness Factors depending upon ingredients. For example, plain popcorn (air-popped popcorn without butter) has a higher FF than popcorn prepared with added butter. The items listed in Table 3 are solid foods. The FF can also be calculated for liquids including various soups and beverages. The FF can be calculated for mixed meals in the same way that the FF is calculated for an individual food. In fact, this is the most practical use of the FF since nearly everyone consumes multiple food items when eating.

Nutritional Benefit

The second factor utilized in food selection according to the present invention is a selectively weighted overall Nutrient Density Rating (NDR) of a food and may be calculated in accordance with the following calculation:

$$NDR = \max(R\text{MIN}, \min(R\text{MAX}, C00$$

$$+ C01*(\ln(\max(\text{PMIN}, \min(\text{PMAX}, 100*DF0/DF1))) - \ln(\text{PAVG}))+$$

$$C02*(\ln(\max(\text{PMIN}, \min(\text{PMAX}, 100*PR0/PR1))) - \ln(\text{PAVG}))+$$

$$C03*(\ln(\max(\text{PMIN}, \min(\text{PMAX}, 100*VA0/VA1))) - \ln(\text{PAVG}))+$$

$$C04*(\ln(\max(\text{PMIN}, \min(\text{PMAX}, 100*VC0/VC1))) - \ln(\text{PAVG}))+$$

$$C05*(\ln(\max(\text{PMIN}, \min(\text{PMAX}, 100*CA0/CA1))) - \ln(\text{PAVG}))+$$

$$C06*(\ln(\max(\text{PMIN}, \min(\text{PMAX}, 100*FE0/FE1))) - \ln(\text{PAVG}))+$$

$$C07*(\ln(\max(\text{PMIN}, \min(\text{PMAX}, 110*VD0/VD1))) - \ln(\text{PAVG}))+$$

$$C08*(\ln(\max(\text{PMIN}, \min(\text{PMAX}, 100*VE0/VE1))) - \ln(\text{PAVG}))+$$

$$C09*(\ln(\max(\text{PMIN}, \min(\text{PMAX}, 100*VK0/VK1))) - \ln(\text{PAVG}))+$$

$$C10*(\ln(\max(\text{PMIN}, \min(\text{PMAX}, 100*TH0/TH1))) - \ln(\text{PAVG}))+$$

$$C11*(\ln(\max(\text{PMIN}, \min(\text{PMAX}, 100*RI0/RI1))) - \ln(\text{PAVG}))+$$

$$C12*(\ln(\max(\text{PMIN}, \min(\text{PMAX}, 100*NI0/NI1))) - \ln(\text{PAVG}))+$$

$$C13*(\ln(\max(\text{PMIN}, \min(\text{PMAX}, 100*VB60/VB61))) - \ln(\text{PAVG}))+$$

$$C14*(\ln(\max(\text{PMIN}, \min(\text{PMAX}, 100*FO0/FO1))) - \ln(\text{PAVG}))+$$

$$C15*(\ln(\max(\text{PMIN}, \min(\text{PMAX}, 100*VB120/VB121))) - \ln(\text{PAVG}))+$$

$$C16*(\ln(\max(\text{PMIN}, \min(\text{PMAX}, 100*PA0/PA1))) - \ln(\text{PAVG}))+$$

$$C17*(\ln(\max(\text{PMIN}, \min(\text{PMAX}, 100*MG0/MG1))) - \ln(\text{PAVG}))+$$

$$C18*(\ln(\max(\text{PMIN}, \min(\text{PMAX}, 100*P0/P1))) - \ln(\text{PAVG}))+$$

$$C19*(\ln(\max(\text{PMIN}, \min(\text{PMAX}, 100*K0/K1))) - \ln(\text{PAVG}))+$$

$$C20*(\ln(\max(\text{PMIN}, \min(\text{PMAX}, 100*ZN0/ZN1))) - \ln(\text{PAVG}))+$$

$$C21*(\ln(\max(\text{PMIN}, \min(\text{PMAX}, 100*CU0/CU1))) - \ln(\text{PAVG}))+$$

$$C22*(\ln(\max(\text{PMIN}, \min(\text{PMAX}, 100*MN0/MN1))) - \ln(\text{PAVG}))+$$

$$C23*(\ln(\max(\text{PMIN}, \min(\text{PMAX}, 100*SE0/SE1))) - \ln(\text{PAVG}))+$$

$$C24*(\ln(\max(\text{PMIN}, \min(\text{PMAX}, 100*SF0/SF1))) - \ln(\text{PAVG}))+$$

$$C25*(\ln(\max(\text{PMIN}, \min(\text{PMAX}, 100*CH0/CH1))) - \ln(\text{PAVG}))+$$

$$C26*(\ln(\max(\text{PMIN}, \min(\text{PMAX}, 100*NA0/NA1))) - \ln(\text{PAVG}))+$$

$$C27*(\ln(\max(\text{PMIN}, \min(\text{PMAX}, 100*SA0/SA1))) - \ln(\text{PAVG}))))$$

where:

$\ln(x)$ is a function that returns the natural (base e) log of the number x $\max(x,y)$ is a function that returns the maximum of either x or y $\min(x,y)$ is a function that returns the minimum of either x or y DF0 is the amount of Dietary Fiber present in a serving.

DF1 is the amount of Dietary Fiber specified as the Daily Value by the US FDA.

PR0 is the amount of Protein present in a serving.

PR1 is the amount of Protein specified as the Daily Value by the US FDA.

(Note: In the preferred embodiment, the amount of protein in the serving is calculated as the total protein times the calculated protein quality, which is equal to the percentage of individual amino acids present in the sample as compared to the optimal standards for amino acid content as presented by the Institute of Medicine. Protein quality has a typical range of 0 to 100%. If individual amino acid content is not known, a protein quality of 50% is used for this calculation.)

VA0 is the amount of Vitamin A present in a serving.

VA1 is the amount of Vitamin A specified as the Daily Value by the US FDA.

VC0 is the amount of Vitamin C present in a serving.

VC1 is the amount of Vitamin C specified as the Daily Value by the US FDA.

CA0 is the amount of Calcium present in a serving.

CA1 is the amount of Calcium specified as the Daily Value by the US FDA.

FE0 is the amount of Iron present in a serving.

FE1 is the amount of Iron specified as the Daily Value by the US FDA.

VD0 is the amount of Vitamin D present in a serving.

VD1 is the amount of Vitamin D specified as the Daily Value by the US FDA.

VE0 is the amount of Vitamin E present in a serving.

VE1 is the amount of Vitamin E specified as the Daily Value by the US FDA.

VK0 is the amount of Vitamin K present in a serving.

VK1 is the amount of Vitamin K specified as the Daily Value by the US FDA.

TH0 is the amount of Thiamin present in a serving.

TH1 is the amount of Thiamin specified as the Daily Value by the US FDA.

RI0 is the amount of Riboflavin present in a serving.

RI1 is the amount of Riboflavin specified as the Daily Value by the US FDA.

NI0 is the amount of Niacin present in a serving.

NI1 is the amount of Niacin specified as the Daily Value by the US FDA.

VB60 is the amount of Vitamin B6 present in a serving.

VB61 is the amount of Vitamin B6 specified as the Daily Value by the US FDA.

FO0 is the amount of Folate present in a serving.

FO1 is the amount of Folate specified as the Daily Value by the US FDA.

VB120 is the amount of Vitamin B12 present in a serving.

VB121 is the amount of Vitamin B12 specified as the Daily Value by the US FDA.

PA0 is the amount of Pantothenic Acid present in a serving.

PA1 is the amount of Pantothenic Acid specified as the Daily Value by the US FDA.

MG0 is the amount of Magnesium present in a serving.

MG1 is the amount of Magnesium specified as the Daily Value by the US FDA.

P0 is the amount of Phosphorus present in a serving.

P1 is the amount of Phosphorus specified as the Daily Value by the US FDA.

K0 is the amount of Potassium present in a serving.

K1 is the amount of Potassium specified as the Daily Value by the US FDA.

ZN0 is the amount of Zinc present in a serving.

ZN1 is the amount of Zinc specified as the Daily Value by the US FDA.

CU0 is the amount of Copper present in a serving.

CU1 is the amount of Copper specified as the Daily Value by the US FDA.

MN0 is the amount of Manganese present in a serving.

MN1 is the amount of Manganese specified as the Daily Value by the US FDA.

SE0 is the amount of Selenium present in a serving.

SE1 is the amount of Selenium specified as the Daily Value by the US FDA.

SF0 is the amount of Saturated Fat present in a serving.

SF1 is the amount of Saturated Fat specified as the Daily Value by the US FDA.

CH0 is the amount of Cholesterol present in a serving.

CH1 is the amount of Cholesterol specified as the Daily Value by the US FDA.

NA0 is the amount of Sodium present in a serving.

NA1 is the amount of Sodium specified as the Daily Value by the US FDA.

SA0 is the number of Calories in a serving derived from sugar and alcohol.

SA1 is the total number of Calories in a serving.

(For the NDR calculation, a "serving" refers to the smallest amount of the analyzed food that will provide either 200 total Calories or 1000 grams of total food weight. "Amount" refers to the measured weight of the nutrient or its Daily Value, and is often expressed in grams, milligrams, or micrograms.)

RMIN, RMAX, PMIN, PMAX, PAVG, and C00 are constants

C01 thru C27 are coefficients that weight the effects of the individual nutrients on the NDR. (For the preferred embodiment, higher weights are assigned to those nutrients that are most commonly known for all foods—i.e. the set of nutrients that are required to appear on a US FDA-approved Nutrition Facts label.)

In the preferred embodiment, these constants and coefficients have the following values:

RMIN=0.0

RMAX=5.0

PMIN=2.5

PMAX=40

PAVG=10

C00=3.0

C01=0.238

C02=0.238

C03=0.238

C04=0.238

C05=0.238

C06=0.238

C07=0.0238

C08=0.0238

C09=0.0238

$C10=0.0238$ $C11=0.0238$ $C12=0.0238$ $C13=0.0238$ $C14=0.0238$ $C15=0.0238$ $C16=0.0238$ $C17=0.0238$ $C18=0.0238$ $C19=0.0238$ $C20=0.0238$ $C21=0.0238$ $C22=0.0238$ $C23=0.0238$ $C24=-0.238$ $C25=-0.238$ $C26=-0.238$ $C27=-0.238$

If the FDA establishes Daily Values for any additional nutrients, these additions may also be incorporated into this calculation.

EXAMPLE

FF and NDR Calculations for FIG. 1

The food product represented by the Nutrition Facts Label shown in FIG. 1 may be used to illustrate the NDR and FF computations. Taking the data from the label the formulae yield the following for eggplant cooked with salt:

$$FF = \max(0.5, \min(5.0, 37/60$$
$$+ 2500/60 * \max(30, 35.4)^{\wedge}(-0.7)$$
$$+ 3/60 * \min(30,1)^{\wedge}1 + 1/1620 * \min(12,2)^{\wedge}3$$
$$- 1/138000 * \min(50,0)^{\wedge}3))$$
$$= 4.1$$

$$NDR = \max(0 \min(5.0, 3.0$$
$$+ 0.238*(\ln(\max(2.5,\min(40,100*11.4/25)))-\ln(10))$$
$$+ 0.238*(\ln(\max(2.5,\min(40,100*2.9/50)))-\ln(10))$$
$$+ 0.238*(\ln(\max(2.5,\min(40,100*286/5000)))-\ln(10))$$
$$+ 0.238*(\ln(\max(2.5,\min(40,100*6.9/60)))-\ln(10))$$
$$+ 0.238*(\ln(\max(2.5,\min(40,100*57.1/1000)))-\ln(10))$$
$$+ 0.238*(\ln(\max(2.5,\min(40,100*1.0/18)))-\ln(10))$$
$$+ 0.0238*(\ln(\max(2.5,\min(40,100*0/400)))-\ln(10))$$
$$+ 0.0238*(\ln(\max(2.5,\min(40,100*0/30)))-\ln(10))$$
$$+ 0.0238*(\ln(\max(2.5,\min(40,100*0/80)))-\ln(10))$$
$$+ 0.0238*(\ln(\max(2.5,\min(40,100*0/1.5)))-\ln(10))$$
$$+ 0.0238*(\ln(\max(2.5,\min(40,100*0/1.7)))-\ln(10))$$
$$+ 0.0238*(\ln(\max(2.5,\min(40,100*0/20)))-\ln(10))$$
$$+ 0.0238*(\ln(\max(2.5,\min(40,100*0/2.0)))-\ln(10))$$
$$+ 0.0238*(\ln(\max(2.5,\min(40,100*0/400)))-\ln(10))$$
$$+ 0.0238*(\ln(\max(2.5,\min(40,100*0/6.0)))-\ln(10))$$
$$+ 0.0238*(\ln(\max(2.5,\min(40,100*0/10)))-\ln(10))$$
$$+ 0.0238*(\ln(\max(2.5,\min(40,100*0/400)))-\ln(10))$$
$$+ 0.0238*(\ln(\max(2.5,\min(40,100*0/1000)))-\ln(10))$$
$$+ 0.0238*(\ln(\max(2.5,\min(40,100*0/3500)))-\ln(10))$$
$$+ 0.0238*(\ln(\max(2.5,\min(40,100*0/15)))-\ln(10))$$
$$+ 0.0238*(\ln(\max(2.5,\min(40,100*0/2.0)))-\ln(10))$$
$$+ 0.0238*(\ln(\max(2.5,\min(40,100*0/2.0)))-\ln(10))$$
$$+ 0.0238*(\ln(\max(2.5,\min(40,100*0/70)))-\ln(10))$$
$$- 0.238*(\ln(\max(2.5,\min(40,100*0/20)))-\ln(10))$$
$$- 0.238*(\ln(\max(2.5,\min(40,100*0/300)))-\ln(10))$$
$$- 0.238*(\ln(\max(2.5,\min(40,100*1353/2400)))-\ln(10))$$
$$- 0.238*(\ln(\max(2.5,\min(40,100*68.4/200)))-\ln(10))))$$

$NDR=2.3$

Current US FDA Daily Values
Calories: 2000
Total Fat: 65 g
Saturated Fat: 20 g
Cholesterol: 300 mg
Total Carbohydrate: 300 g
Dietary Fiber: 25 g
Protein: 50 g
Vitamin A: 5000 IU
Vitamin C: 60 mg
Vitamin D: 400 IU
Vitamin E: 30 IU
Vitamin K: 80 mcg
Thiamin: 1.5 mg
Riboflavin: 1.7 mg
Niacin: 20 mg
Vitamin B6: 2 mg
Folate: 400 mcg
Vitamin B12: 6 mcg
Pantothenic Acid: 10 mg
Calcium: 1000 mg
Iron: 18 mg
Magnesium: 400 mg
Phosphorus: 1000 mg
Potassium: 3500 mg
Sodium: 2400 mg
Zinc: 15 mg Copper: 2 mg
Manganese: 2 mg
Selenium: 70 mcg

Nutritional Target Map 'NTM'

Figure 5:
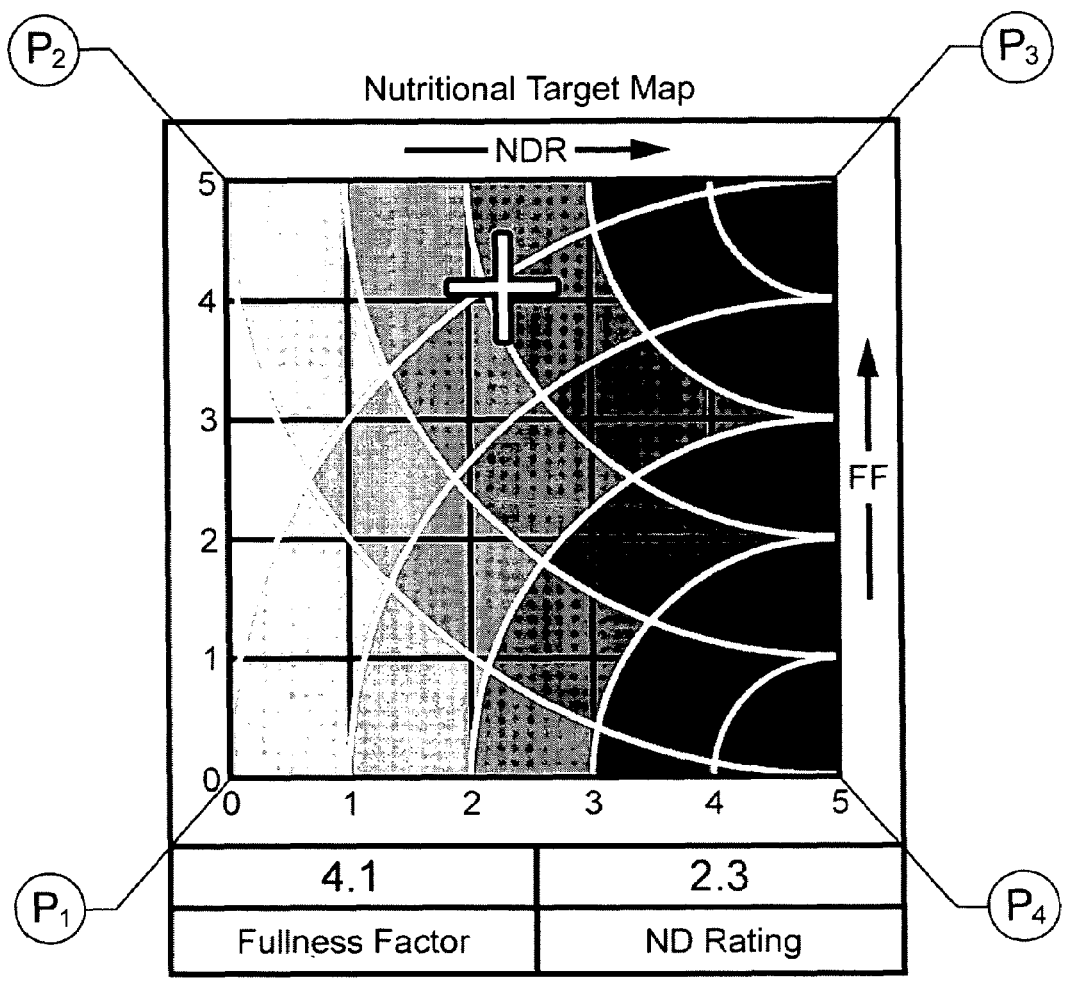
FIG. 5 is a representation showing the NDR and FF in a graphical format for convenience of understanding and use.

FIG. 5 shows one example of a graphical representation or map of the NDR and the FF. To understand the Nutritional Target Map, it may be considered as overlapping targets. One target is for the benefit of the individuals trying to lose weight. Foods in the region that appear closer to $P_3$ are foods that tend to be more supportive of healthy weight loss. In a similar matter, the target helps identify foods that tend to be more supportive of healthy weight gain as being closer to $P_4$. Conversely, foods in the region closest to $P_1$ tend to be the least supportive to weight loss, and the foods in the region closest to $P_2$ tend to be the least supportive of weight gain. The plus sign marks the NDR and FF for the food that was analyzed in the preceding example, in this case the cooked eggplant represented on the Nutrition Facts label of FIG. 1.

Foods with higher FFs are believed to be better for weight loss diets because they are more filling per calorie. Foods with lower FFs are believed to be better for weight gain because they are less filling per calorie.

Foods with higher NDRs appear closer to one margin of the graph, while foods with lower NDRs appear closer to the opposite margin. Foods with higher NDRs are believed to provide more nutritional benefits while ones with lower NDRs are believed to provide less nutritional benefits.

Foods in the region defined by higher FFs and the higher NDRs are believed to be better for healthy weight loss supporting the consumption of more nutrients with less calories.

Foods in the region defined by lower FFs and higher NDRs are believed to be better for healthy weight gain supporting the consumption of more nutrients and more calories.

The NTM may be visually interpreted to include separately discernable regions that correspond to particular food groupings. For example, consider the following region definitions:
Region 1, to include foods most proximate to point $P_1$:
Not filling or nutritious
(e.g. candies, cakes, butter, cooking oil)
Region 2, to include foods most proximate to point $P_2$:
Filling, but not nutritious
(e.g. coffee, tea, gelatin)
Region 3, to include foods most proximate to point $P_3$:
Filling and nutritious
(e.g. fresh fruits and vegetables)
Region 4, to include foods most proximate to point $P_4$:
Nutritious, but not filling
(e.g. nuts, seeds, vitamin-enriched cereals)

Figure 6:
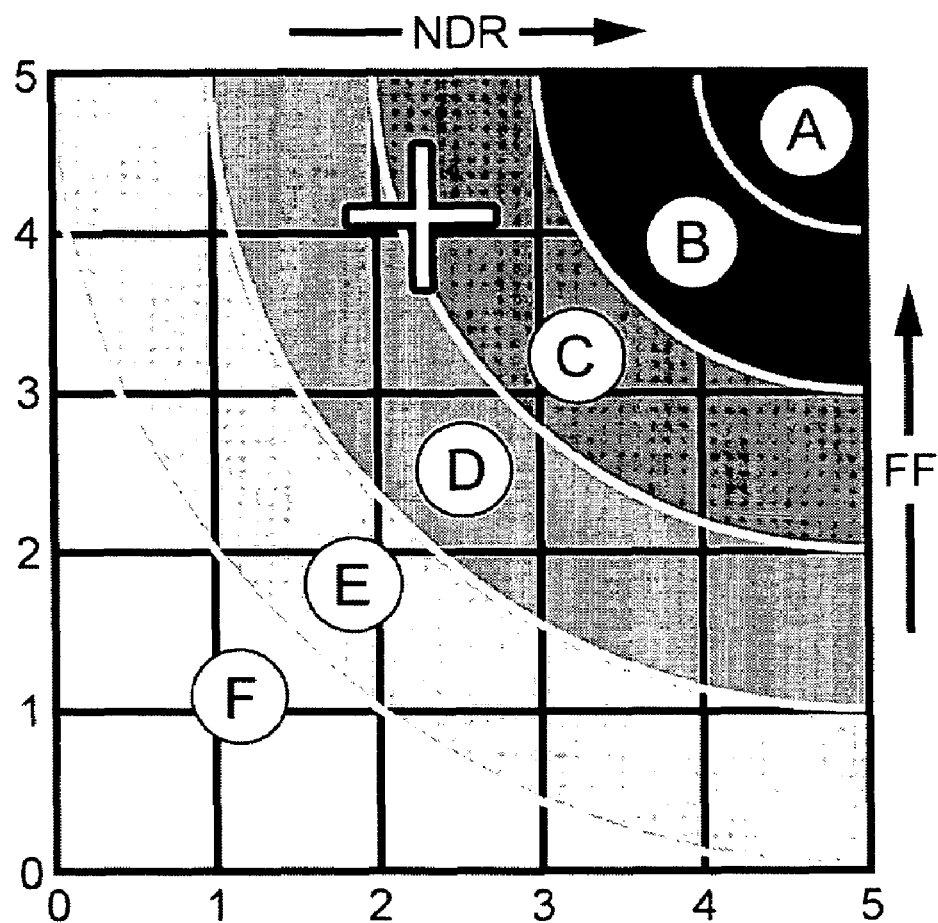
FIGS. 6 and 7 show other graphical representations of the factors specific to healthy weight loss and healthy weight gain respectively.
Figure 7:
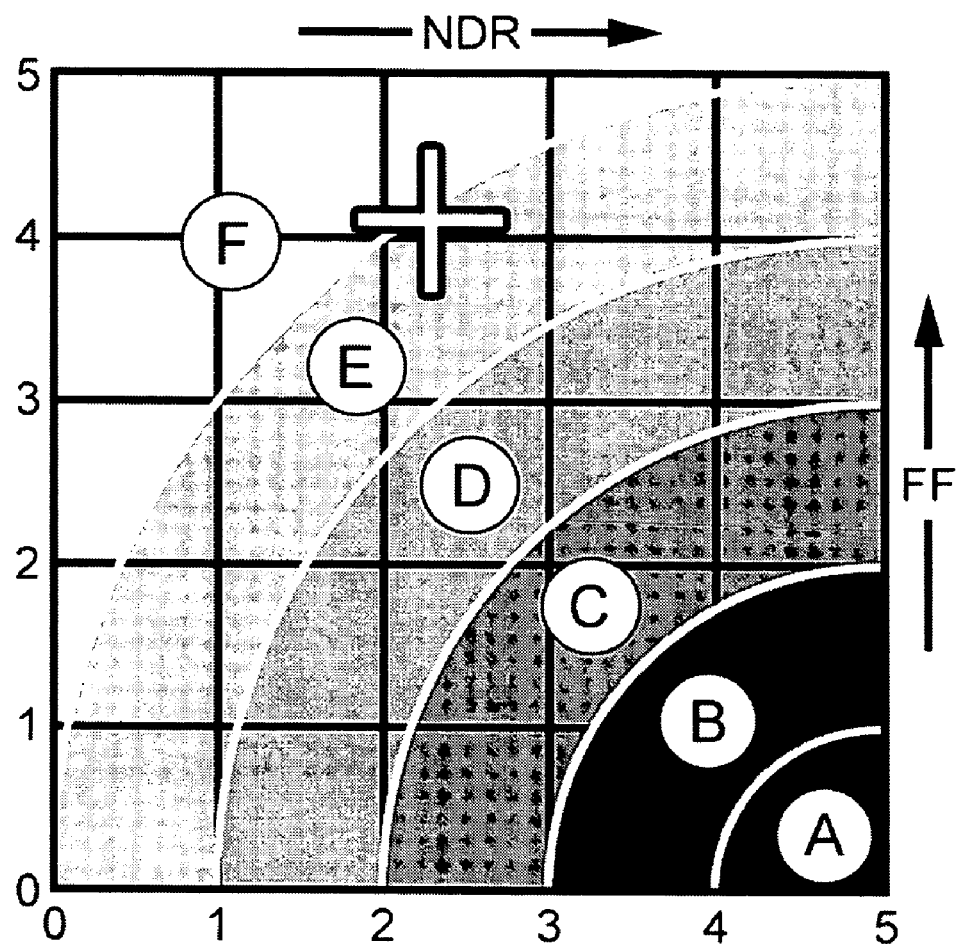

FIGS. 6 and 7 help illustrate additional calculations in which the FF and NDR can be further combined through calculation to yield a single number (or equivalent nomenclature) that reflects the food's level of suitability for a particular goal.

For example, to select foods for healthy weight loss, one would seek foods closest to point $P_3$. The distance from the food to point $P_3$ can be represented mathematically by the equation:

$$D_3 = ((5-FF)^2 + (5-NDR)^2)^{0.5}$$

Condensing the food's FF and NDR into a single number simplifies its reporting in applications where the Nutritional Target Map would be hard to reproduce (e.g. within tables of multiple foods in a diet book). It also makes the results of this method more understandable to certain individuals who don't have need for the individual FF and NDR numbers or appreciate the complexity of the NTM.

As FIG. 6 shows, this calculated distance can also be equated to and identified via a fixed number of discrete levels (labeled A-F), which correspond to the shaded bands in this alternate embodiment.

The same applies to FIG. 7, except that the distance calculation is:

$$D_4 = (FF^2 + (5-NDR)^2)^{0.5}$$

FIGS. 6 and 7 apply to the preferred embodiments of the method for selecting foods for healthy weight loss and healthy weight gain. With respect to these embodiments, the food product of FIG. 1 (eggplant, cooked with salt) is a level "C" for healthy weight loss and a level "E" for healthy weight gain. Other similar embodiments or interpretations will be apparent to those skilled in the art.

Thus, an individual can select foods consistent with that individual's health and dietary goals by referring to the NTM. The NTM can be generated for any food because it relies on the very same set of nutrients that appear on the Nutrition Facts label of FIG. 1. This means an individual can use the NTM to analyze any food from most any source.

The particular format may be varied to present to visual guidelines to assist individuals. The preferred format is a map or graph format. It is to be understood that the FF and NDR factors may be calculated manually or by use of a computer using software or an algorithm. Similarly, the calculated factors could then be displayed by the computer indicating the appropriateness of the food for the individual's dietary goals.

The present system gives an individual the tools needed to consistently and accurately evaluate the individual's diet. It is up to the individual to plan meals and assume responsibility for the individual's food choices. The diet utilizes NDRs and Fullness Factors. These factors, as discussed above, provide a reasonable scientific prediction of a food's benefit in relation to the diet.

However, in all cases, individuals in establishing goals and working on a program to reach those goals should consult a nutritionist or healthcare professional for specific dietary recommendations.

It will be obvious to those skilled in the art to make various changes, alterations and modifications to the invention described herein. To the extent such changes, alterations and modifications do not depart from the spirit and scope of the appended claims, they are intended to be encompassed therein.

I claim:
1. A method of rating food, comprising the steps of:
   (a) calculating a first factor FF that represents an estimate of the satiating effect of a food according to the relationship:

FF=max(FFMIN,min(FFMAX,C00

+C01*max(CALMIN,CAL)^E01

+C02*min(PRMAX,PR)^E02

+C03*min(DFMAX,DF)^E03

+C04*min(TFMAX,TF)^E04))

where:
   max(CALMIN,CAL) is a function that returns the maximum of either CALMIN or CAL,
   min(PRMAX,PR) is a function that returns the minimum of either PRMAX or PR, min(DFMAX,DF) is a function that returns the minimum of either DFMAX or DF, min(TFMAX,TF) is a function that returns the minimum of either TFMAX or TF, max(FFMIN,min(FFMAX,C00+C01*max(CALMIN, CAL)^E1+C02*min(PRMAX,PR)^E02+C03*min(DFMAX,DF)^E03+C04*min(TFMAX,TF)^E04)) is a function that returns the maximum of either (i) FFMIN or (ii) the function that returns the minimum of either FFMAX or the quantity C00+C01*max(CALMIN, CAL)^E01+C02*min(PRMAX,PR)^E02+C03*min(DFMAX,DF)^E03+C04*min(TFMAX,TF)^04

CAL is total Calories per 100 gram portion of the food,

PR is grams of Protein per 100 g,

DF is grams Dietary Fiber per 100 g, and

TF is grams total Fat per 100 g;

FFMIN, FFMAX, CALMIN, PRMAX, DFMAX, TFMAX, and C00 are constants, C01 through C04 are coefficients, and E01 through E04 are exponential powers having the approximate following values:

FFMIN=0.5
FFMAX=5.0
CALMIN=30
DFMAX=12
C03=1/1620
C04=−1/138,000
E02=1.0
E04=3.0;

(b) calculating a second factor NDR that represents the nutritional benefit of said food according to the relationship:

NDR=max($R$MIN,min($R$MAX,C00

+C01*(ln(max(PMIN,min(PMAX,100*DF0/DF1)))−ln(PAVG))

+C02*(ln(max(PMIN,min(PMAX,100*PR0/PR1)))−ln(PAVG))

+C03*(ln(max(PMIN,min(PMAX,100*VA0/VA1)))−ln(PAVG))

+C04*(ln(max(PMIN,min(PMAX,100*VC0/VC1)))−ln(PAVG))

+C05*(ln(max(PMIN,min(PMAX,100*CA0/CA1)))−ln(PAVG))

+C06*(ln(max(PMIN,min(PMAX,100*FE0/FE1)))−ln(PAVG))

+C07*(ln(max(PMIN,min(PMAX,100*VD0/VD1)))−ln(PAVG))

+C08*(ln(max(PMIN,min(PMAX,100*VE0/VE1)))−ln(PAVG))

+C09*(ln(max(PMIN,min(PMAX,100*VK0/VK1)))−ln(PAVG))

+C10*(ln(max(PMIN,min(PMAX,100*TH0/TH1)))−ln(PAVG))

+C11*(ln(max(PMIN,min(PMAX,100*RI0/RI1)))−ln(PAVG))

+C12*(ln(max(PMIN,min(PMAX,100*NI0/NI1)))−ln(PAVG))

+C13*(ln(max(PMIN,min(PMAX,100*VB60/VB61)))−ln(PAVG))

+C14*(ln(max(PMIN,min(PMAX,100*FO0/FO1)))−ln(PAVG))

+C15*(ln(max(PMIN,min(PMAX,100*VB120/VB121)))−ln(PAVG))

+C16*(ln(max(PMIN,min(PMAX,100*PA0/PA1)))−ln(PAVG))

+C17*(ln(max(PMIN,min(PMAX,100*MG0/MG1)))−ln(PAVG))

+C18*(ln(max(PMIN,min(PMAX,100*P0/P1)))−ln(PAVG))

+C19*(ln(max(PMIN,min(PMAX,100*K0/K1)))−ln(PAVG))

+C20*(ln(max(PMIN,min(PMAX,100*ZN0/ZN1)))−ln(PAVG))

+C21*(ln(max(PMIN,min(PMAX,100*CU0/CU1)))−ln(PAVG))

+C22*(ln(max(PMIN,min(PMAX,100*MN0/MN1)))−ln(PAVG))

+C23*(ln(max(PMIN,min(PMAX,100*SE0/SE1)))−ln(PAVG))

+C24*(ln(max(PMIN,min(PMAX,100*SF0/SF1)))−ln(PAVG))

+C25*(ln(max(PMIN,min(PMAX,100*CH0/CH1)))−ln(PAVG))

+C26*(ln(max(PMIN,min(PMAX,100*NA0NA1)))−ln(PAVG))

+C27*(ln(max(PMIN,min(PMAX,100*SA0/SA1)))−ln(PAVG))))

where:

ln is the natural (base e) logarithm, max(PMIN,min(PMAX,100*DF0/DF1)) is a function that returns the maximum of either (i) PMIN or (ii) the function that returns the minimum of either PMAX or 100*DF0/DF1, max(PMIN min(PMAX,100*PR0/PR1)) is a function that returns the maximum of either (i) PMIN or (ii) the function that returns the minimum of either PMAX or 100*PR0/PR1, max(PMIN min(PMAX,100*VA0/VA1)) is a function that returns the maximum of either (i) PMIN or (ii) the function that returns the minimum of either PMAX or 100*VA0/VA1, max(PMIN,min(PMAX,100*VC0/VC1)) is a function that returns the maximum of either (i) PMIN or (ii) the function that returns the minimum of either PMAX or 100*VC0/VC1, max(PMIN,min(PMAX,100*CA0/CA1)) is a function that returns the maximum of either (i) PMIN or (ii) the function that returns the minimum of either PMAX or 100*CA0/CA1, max(PMIN,min(PMAX,100*FE0/FE1)) is a function that returns the maximum of either (i) PMIN or (ii) the function that returns the minimum of either PMAX or 100*FE0/FE1, max(PMIN min(PMAX,100*VD0/VD1)) is a function that returns the maximum of either (i) PMIN or (ii) the function that returns the minimum of either PMAX or 100*VD0/VD1, max(PMIN,min(PMAX,100*VE0/VE1)) is a function that returns the maximum of either (i) PMIN or (ii) the function that returns the minimum of either PMAX or 100*VE0/VE1, max(PMIN,min(PMAX,100*VK0/VK1)) is a function that returns the maximum of either (i) PMIN or (ii) the function that returns the minimum of either PMAX or 100*VK0/VK1, max(PMIN,min(PMAX,100*TH0/TH1)) is a function that returns the maximum of either (i) PMIN or (ii) the function that returns the minimum of either PMAX or 100*TH0/TH1, max(PMIN,min(PMAX,100*RI0/RI1)) is a function that returns the maximum of either (i) PMIN or (ii) the function that returns the minimum of either PMAX or 100*RI0/RI1, max(PMIN,min(PMAX,100*NI0/NI1)) is a function that returns the maximum of either (i) PMIN or (ii) the function that returns the minimum of either PMAX or 100*NI0/NI1, max(PMIN,min(PMAX,100*VB60/VB61)) is a function that returns the maximum of either (i) PMIN or (ii) the function that returns the minimum of either PMAX or 100*VB60/VB61, max(PMIN,min(PMAX,100*FO0/FO1)) is a function that returns the maximum of either (i) PMIN or (ii) the function that returns the minimum of either PMAX or 100*FO0/FO1, max(PMIN,min(PMAX,100*VB120/VB121)) is a function that returns the maximum of either (i) PMIN or (ii) the function that returns the minimum of either PMAX or 100*VB120/VB121, max(PMIN,min(PMAX,100*PA0/PA1)) is a function that returns the maximum of either (i) PMIN or (ii) the function that returns the minimum of either PMAX or 100*PA0/PA1, max(PMIN,min(PMAX,100*MG0/MG1)) is a function that returns the maximum of either (i) PMIN or (ii) the function that returns the minimum of either PMAX or 100*MG0/MG1, max(PMIN,min(PMAX,100*P0/P1)) is a function that returns the maximum of either (i) PMIN or (ii) the function that returns the minimum of either PMAX or 100*P0/P1, max(PMIN,min(PMAX,100*K0/K1)) is a function that returns the maximum of either (i) PMIN or (ii) the function that returns the minimum of either PMAX or 100*K0/K1, max(PMIN,min(PMAX,100*ZN0/ZN1)) is a function that returns the maximum of either (i) PMIN or (ii) the function that returns the minimum of either PMAX or 100*ZN0/ZN1, max(PMIN,min(PMAX,100*CU0/CU1)) is a function that returns the maximum of either (i) PMIN or (ii) the function that returns the minimum of either PMAX or 100*CU0/CU1, max(PMIN,min(PMAX,100*MN0/MN1)) is a function that returns the maximum of either (i) PMIN or (ii) the function that returns the minimum of either PMAX or 100*MN0/MN1, max(PMIN,min(PMAX,100*SE0/SE1)) is a function that returns the maximum of either (i) PMIN or (ii) the function that returns the minimum of either PMAX or 100*SE0/SE1, max(PMIN,min(PMAX,100*SF0/SF1)) is a function that returns the maximum of either (i) PMIN or (ii) the function that returns the minimum of either PMAX or 100*SF0/SF1, max(PMIN,min(PMAX,100*CH0/CH1)) is a function that returns the maximum of either (i) PMIN or (ii) the function that returns the minimum of either PMAX or 100*CH0/CH1, max(PMIN,min(PMAX,100*NA0/NA1)) is a function that returns the maximum of either (i) PMIN or (ii) the function that returns the minimum of either PMAX or 100*NA0/NA1, max(PMIN,min(PMAX,100*SA0/SA1)) is a function that returns the maximum of either (i) PMIN or (ii) the function that returns the minimum of either PMAX or 100*SA0/SA1, max(RMIN,min(RMAX,C00+C01*(ln(max(PMIN,min(PMAX,100*DF0/DF1)))−ln(PAVG))+C02*(ln(max(PMIN,min(PMAX,100*PR0/PR1)))−ln(PAVG))+C03*(ln(max(PMIN,min(PMAX,100*VA0/VA1)))−ln(PAVG))+C04*(ln(max(PMIN,min(PMAX,100*VC0/VC1)))−ln(PAVG))+C05*(ln(max(PMIN,min(PMAX,100*CA0/CA1)))−ln(PAVG))+C06*(ln(max(PMIN,min(PMAX,100*FE0/FE1)))−ln(PAVG))+C07*(ln(max(PMIN,min(PMAX,100*VD0/VD1)))−ln(PAVG))+C08*(ln(max(PMIN,min(PMAX,100*VE0/VE1)))−ln(PAVG))+C09*(ln(max(PMIN,min(PMAX,100*VK0/VK1)))−ln(PAVG))+C10*(ln(max(PMIN,min(PMAX,100*TH0/TH1)))−ln(PAVG))+C11*(ln(max(PMIN,min(PMAX,100*RI0/RI1)))−ln(PAVG))+C12*(ln(max(PMIN,min(PMAX,100*NI0/NI1)))−ln(PAVG))+C13*(ln(max(PMIN,min(PMAX,100*VB60/VB61)))−ln(PAVG))+C14*(ln(max(PMIN,min(PMAX,100*FO0/FO1)))−ln(PAVG))+C15*(ln(max(PMIN,min(PMAX,100*VB120/VB121)))−ln(PAVG))+C16*(ln(max(PMIN,min(PMAX,100*PA0/PA1)))−ln(PAVG))+C17*(ln(max(PMIN,min(PMAX,100*MG0/MG1)))−ln(PAVG))+C18*(ln(max(PMIN,min(PMAX,100*P0/P1)))−ln(PAVG))+C19*(ln(max(PMIN,min(PMAX,100*K0/K1)))−ln(PAVG))+C20*(ln(max(PMIN,min(PMAX,100*ZN0/ZN1)))−ln(PAVG))+C21*(ln(max(PMIN,min(PMAX,100*CU0/CU1)))−ln(PAVG))+C22*(ln(max(PMIN,min(PMAX,100*MN0/MN1)))−ln(PAVG))+C23*(ln(max(PMIN,min(PMAX,100*SE0/SE1)))−ln(PAVG))+C24*(ln(max(PMIN,min(PMAX,100*SF0/SF11)))−ln(PAVG))+C25*(ln(max(PMIN,min(PMAX,100*CH0/CH1)))−ln(PAVG))+C26*(ln(max(PMIN,min(PMAX,100*NA0/NA1)))−ln(PAVG))+C27*(ln(max(PMIN,min(PMAX,100*SA0/SA1)))−ln(PAVG)))) is a function that returns the maximum of either (i) RMIN or (ii) the function that returns the minimum of either RMAX or the quantity C00+C01*(ln(max(PMIN,min(PMAX,100*DF0/DF1)))−ln(PAVG))+C02*(ln(max(PMIN,min(PMAX,100*PR0/PR1)))−ln(PAVG))+C03*(ln(max(PMIN,min(PMAX,100*VA0/VA1)))−ln(PAVG))+C04*(ln(max(PMIN,min(PMAX,100*VC0/VC1)))−ln(PAVG))+C05*(ln(max(PMIN,min(PMAX,100*CA0/CA1)))−ln(PAVG))+C06*(ln(max(PMIN,min(PMAX,100*FE0/FE1)))−ln(PAVG))+C07*(ln(max(PMIN,min(PMAX,100*VD0/VD1)))−ln(PAVG))+C08*(ln(max(PMIN,min(PMAX,100*VE0/VE1)))−ln(PAVG))+C09*(ln(max(PMIN,min(PMAX,100*VK0/VK1)))−ln(PAVG))+C10*(ln(max(PMIN,min(PMAX,100*TH0/TH1)))−ln(PAVG))+C11*(ln(max(PMIN,min(PMAX,100*RI0/RI1)))−ln(PAVG))+C12*(ln(max(PMIN,min(PMAX,100*NI0/NI1)))−ln (PAVG))+C13*(ln(max(PMIN,min(PMAX, 100*VB60/VB61)))−ln(PAVG))+C14*(ln(max(PMIN, min(PMAX,100*FO0/FO1)))−ln(PAVG))+C15*(ln (max(PMIN,min(PMAX,100*VB120/VB121)))−ln (PAVG))+C16*(ln(max(PMIN,min(PMAX,100*PA0/ PA1)))−ln(PAVG))+C17*(ln(max(PMIN,min(PMAX, 100*MG0/MG1)))−ln(PAVG))+C18*(ln(max(PMIN, min(PMAX,100*P0/P1)))−ln(PAVG))+C19*(ln(max (PMIN,min(PMAX,100*K0/K1)))−ln(PAVG))+C20* (ln(max(PMIN,min(PMAX,100*ZN0/ZN1)))−ln (PAVG))+C21*(ln(max(PMIN,min(PMAX,100*CU0/ CU1)))−ln(PAVG))+C22*(ln(max(PMIN,min(PMAX, 100*MN0/MN1)))−ln(PAVG))+C23*(ln(max(PMIN, min(PMAX,100*SE0/SE1)))−ln(PAVG))+C24*(ln (max(PMIN,min(PMAX,100*SF0/SF1)))−ln (PAVG))+C25*(ln(max(PMIN,min(PMAX,100*CH0/ CH1)))−ln(PAVG))+C26*(ln(max(PMIN,min(PMAX, 100*NA0/NA1)))−ln(PAVG))+C27*(ln(max(PMIN, min(PMAX,100*SA0/SA1)))−ln(PAVG))

DF0 is the amount of Dietary Fiber present in a serving,
DF1 is the amount of Dietary Fiber specified as the Daily Value by the US FDA;
PR0 is the amount of Protein present in a serving;
PR1 is the amount of Protein specified as the Daily Value by the US FDA;
VA0 is the amount of Vitamin A present in a serving;
VA1 is the amount of Vitamin A specified as the Daily Value by the US FDA;
VC0 is the amount of Vitamin C present in a serving;
VC1 is the amount of Vitamin C specified as the Daily Value by the US FDA;
CA0 is the amount of Calcium present in a serving;
CA1 is the amount of Calcium specified as the Daily Value by the US FDA;
FE0 is the amount of Iron present in a serving;
FE1 is the amount of Iron specified as the Daily Value by the US FDA;
VD0 is the amount of Vitamin D present in a serving;
VD1 is the amount of Vitamin D specified as the Daily Value by the US FDA;
VE0 is the amount of Vitamin E present in a serving;
VE1 is the amount of Vitamin E specified as the Daily Value by the US FDA;
VK0 is the amount of Vitamin K present in a serving;
VK1 is the amount of Vitamin K specified as the Daily Value by the US FDA;
TH0 is the amount of Thiamin present in a serving;
TH1 is the amount of Thiamin specified as the Daily Value by the US FDA;
RI0 is the amount of Riboflavin present in a serving;
RI1 is the amount of Riboflavin specified as the Daily Value by the US FDA;
NI0 is the amount of Niacin present in a serving;
NI1 is the amount of Niacin specified as the Daily Value by the US FDA;
VB60 is the amount of Vitamin B6 present in a serving;
VB61 is the amount of Vitamin B6 specified as the Daily Value by the US FDA;
FO0 is the amount of Folate present in a serving;
FO1 is the amount of Folate specified as the Daily Value by the US FDA;
VB120 is the amount of Vitamin B12 present in a serving;
VB121 is the amount of Vitamin B12 specified as the Daily Value by the US FDA;
PA0 is the amount of Pantothenic Acid present in a serving;
PA1 is the amount of Pantothenic Acid specified as the Daily Value by the US FDA;
MG0 is the amount of Magnesium present in a serving;
MG1 is the amount of Magnesium specified as the Daily Value by the US FDA;
P0 is the amount of Phosphorus present in a serving;
P1 is the amount of Phosphorus specified as the Daily Value by the US FDA;
K0 is the amount of Potassium present in a serving;
K1 is the amount of Potassium specified as the Daily Value by the US FDA;
ZN0 is the amount of Zinc present in a serving;
ZN1 is the amount of Zinc specified as the Daily Value by the US FDA;
CU0 is the amount of Copper present in a serving;
CU1 is the amount of Copper specified as the Daily Value by the US FDA;
MN0 is the amount of Manganese present in a serving;
MN1 is the amount of Manganese specified as the Daily Value by the US FDA;
SE0 is the amount of Selenium present in a serving;
SE1 is the amount of Selenium specified as the Daily Value by the US FDA;
SF0 is the amount of Saturated Fat present in a serving;
SF1 is the amount of Saturated Fat specified as the Daily Value by the US FDA;
CH0 is the amount of Cholesterol present in a serving;
CH1 is the amount of Cholesterol specified as the Daily Value by the US FDA;
NA0 is the amount of Sodium present in a serving;
NA1 is the amount of Sodium specified as the Daily Value by the US FDA;
SA0 is the number of Calories in a serving from sugars (as reported on Nutrition Facts labels) and alcohol; and
SA1 is the total number of Calories in a serving;

wherein:
RMIN, RMAX, PMIN, PMAX, PAVG, and C00 are constants,
C01 thru C27 are coefficients that weight the effects of the individual nutrients on the NDR; and
wherein these constants and coefficients have the following approximate values:
RMIN=0.0
RMAX=5.0
PMAX=40
C00=3.0
C01=0.238
C02=0.238
C03=0.238
C04=0.238
C05=0.238
C06=0.238
C07=0.0238
C08=0.0238
C09=0.0238
C10=0.0238
C11=0.0238
C12=0.0238
C13=0.0238
C14=0.0238
C15=0.0238
C16=0.0238
C17=0.0238
C18=0.0238
C19=0.0238
C20=0.0238
C21=0.0238
C22=0.0238
C23=0.0238

C24=−0.238
C25=−0.238
C26=−0.238
C27=−0.238; and (c) providing to a user a guideline using said first and second factors to enable food selection in accordance with at least one dietary goal;

wherein at least one of steps (a) and (b) is effected using a suitably programmed computer.

2. The method of claim 1, wherein said step of providing to a user a guideline includes plotting said factors NDR and FF on a rectilinear graph.

3. The method of claim 1, wherein said step of providing to a user a guideline includes providing said first and second factors in a visual format.

4. The method of claim 3, wherein said visual format includes regions based on nutritional characteristics of said food.

5. The method of claim 1, wherein said step of providing to a user a guideline includes providing a graphical representation including said first and second factors as coordinates.

6. The method of claim 5, wherein said graphical representation includes regions associated with different ones of said at least one dietary goal.

7. The method of claim 6, further comprising the step of combining said first and second factors into a single indicator corresponding to one of said regions.

8. The method of claim 1, further comprising the step of combining said first and second factors into a single indicator of suitability of said food for at least one dietary goal.

9. A food rating system, comprising:

(a) a data processor adapted to calculate:

(i) a first factor that represents an estimate of the satiating effect of a food according to the relationship:

$$FF = \max(FFMIN, \min(FFMAX, C00$$
$$+C01 * \max(CALMIN, CAL)^{E01}$$
$$+C02 * \min(PRMAX, PR)^{E02}$$
$$+C03 * \min(DFMAX, DF)^{E03}$$
$$+C04 * \min(TFMAX, TF)^{E04}))$$

where:

FF refers to "fullness factor"

max(CALMIN,CAL) is a function that returns the maximum of either CALMIN or CAL, min(PRMAX,PR) is a function that returns the minimum of either PRMAX or PR, min(DFMAX,DF) is a function that returns the minimum of either DFMAX or DF, min(TFMAX,TF) is a function that returns the minimum of either TFMAX or TF, max(FFMIN,min(FFMAX,C00+C01*max(CALMIN,CAL)^E01+C02*min(PRMAX,PR)^E02+C03*min(DFMAX,DF)^E03+C04*min(TFMAX,TF)^E04)) is a function that returns the maximum of either (i) FFMIN or (ii) the function that returns the minimum of either FFMAX or the quantity C00+C01*max(CALMIN,CAL)^E01+C02*min(PRMAX PR)^E02+C03*min(DFMAX,DF)^E03+C04*min(TFMAX,TF)^E04, CAL is total Calories per 100 gram portion of the food,
PR is grams of Protein per 100 g,
DF is grams Dietary Fiber per 100 g, and
TF is grams total Fat per 100 g;

FFMIN, FFMAX, CALMIN, PRMAX, DFMAX, TFMAX, and C00 are constants, C01 through C04 are coefficients, and E01 through E04 are exponential powers having the approximate following values:

FFMIN=0.5
FFMAX=5.0
CALMIN=30
PRMAX=30
DFMAX=12
TFMAX=50
C00=37/60
C01=2500/60
C02=3/60
C03=1/1620
C04=−1/138,000
E01=−0.7
E02=1.0
E03=3.0
E04=3.0; and (ii) a second factor that represents the nutritional benefit of said food according to the relationship:

$$NDR = \max(R\text{MIN}, \min(R\text{MAX}, C00$$

$$+C01*(\ln(\max(PMIN,\min(PMAX,100*DF0/DF1)))-\ln(PAVG))$$

$$+C02*(\ln(\max(PMIN,\min(PMAX,100*PR0/PR1)))-\ln(PAVG))$$

$$+C03*(\ln(\max(PMIN,\min(PMAX,100*VA0/VA1)))-\ln(PAVG))$$

$$+C04*(\ln(\max(PMIN,\min(PMAX,100*VC0/VC1)))-\ln(PAVG))$$

$$+C05*(\ln(\max(PMIN,\min(PMAX,100*CA0/CA1)))-\ln(PAVG))$$

$$+C06*(\ln(\max(PMIN,\min(PMAX,100*FE0/FE1)))-\ln(PAVG))$$

$$+C07*(\ln(\max(PMIN,\min(PMAX,100*VD0/VD1)))-\ln(PAVG))$$

$$+C08*(\ln(\max(PMIN,\min(PMAX,100*VE0/VE1)))-\ln(PAVG))$$

$$+C09*(\ln(\max(PMIN,\min(PMAX,100*VK0/VK1)))-\ln(PAVG))$$

$$+C10*(\ln(\max(PMIN,\min(PMAX,100*TH0/TH1)))-\ln(PAVG))$$

$$+C11*(\ln(\max(PMIN,\min(PMAX,100*RI0/RI1)))-\ln(PAVG))$$

$$+C12*(\ln(\max(PMIN,\min(PMAX,100*NI0/NI1)))-\ln(PAVG))$$

$$+C13*(\ln(\max(PMIN,\min(PMAX,100*VB60/VB61)))-\ln(PAVG))$$

$$+C14*(\ln(\max(PMIN,\min(PMAX,100*FO00/FO1)))-\ln(PAVG))$$

$$+C15*(\ln(\max(PMIN,\min(PMAX,100*VB120/VB121)))-\ln(PAVG))$$

$$+C16*(\ln(\max(PMIN,\min(PMAX,100*PA0/PA1)))-\ln(PAVG))$$

$$+C17*(\ln(\max(PMIN,\min(PMAX,100*MG0/MG1)))-\ln(PAVG))$$

$$+C18*(\ln(\max(PMIN,\min(PMAX,100*P0/P1)))-\ln(PAVG))$$

$$+C19*(\ln(\max(PMIN,\min(PMAX,00*K0/K1)))-\ln(PAVG))$$

$$+C20*(\ln(\max(PMIN,\min(PMAX,100*ZN0/ZN1)))-\ln(PAVG))$$

$$+C21*(\ln(\max(PMIN,\min(PMAX,100*CU0/CU1)))-\ln(PAVG))$$

$$+C22*(\ln(\max(PMIN,\min(PMAX,100*MN0/MN1)))-\ln(PAVG))$$

$$+C23*(\ln(\max(PMIN,\min(PMAX,100*SE0/SE1)))-\ln(PAVG))$$

$$+C24*(\ln(\max(PMIN,\min(PMAX,100*SF0/SF1)))-\ln(PAVG))$$

$$+C25*(\ln(\max(PMIN,\min(PMAX,100*CH0/CH1)))-\ln(PAVG))$$

$$+C26*(\ln(\max(PMIN,\min(PMAX,100*NA0/NA1)))-\ln(PAVG))$$

$$+C27*(\ln(\max(PMIN,\min(PMAX,100*SA0/SA1)))-\ln(PAVG))))$$

where:

NDR refers to "nutrient density"

ln is the natural (base e) logarithm, max(PMIN,min(PMAX,100*DF0/DF1) is a function that returns the maximum of either (i) PMIN or (ii) the function that returns the minimum of either PMAZ or 100*DF0/DF1, max(PMIN,min(PMAZ,100*PR0/PR1)) is a function that returns the maximum of either (i) PMIN or (ii) the function that returns the minimum of either PMAX or 100*PR0/PR1, max(PMIN,min(PMAX,100*VA0/VA1)) is a function that returns the maximum of either (i) PMIN or (ii) the function that returns the minimum of either PMAX or 100*VA0/VA1, max(PMIN min(PMAX,100*VC0/VC1)) is a function that returns the maximum of either (i) PMIN or (ii) the function that returns the minimum of either PMAX or 100*VC0/VC1, max(PMIN,min(PMAX,100*CA0/CA1)) is a function that returns the maximum of either (i) PMIN or (ii) the function that returns the minimum of either PMAX or 100*CA0/CA1, max(PMIN,min(PMAX,100*FE0/FE1)) is a function that returns the maximum of either (i) PMIN or (ii) the function that returns the minimum of either PMAX or 100*FE0/FE1, max(PMIN,min(PMAX,100*VD0/VD1)) is a function that returns the maximum of either (i) PMIN or (ii) the function that returns the minimum of either PMAX or 100*VD0/VD1, max(PMIN,min(PMAX,100*VE0/VE1)) is a function that returns the maximum of either (i) PMIN or (ii) the function that returns the minimum of either PMAX or 100*VE0/VE1, max(PMIN,min(PMAX,100*VK0/VK1)) is a function that returns the maximum of either (i) PMIN or (ii) the function that returns the minimum of either PMAX or 100*VK0/VK1, max(PMIN,min(PMAX,100*TH0/TH1)) is a function that returns the maximum of either (i) PMIN or (ii) the function that returns the minimum of either PMAX or 100*TH0/TH1, max(PMIN,min(PMAX,100*RI0/RI1)) is a function that returns the maximum of either (i) PMIN or (ii) the function that returns the minimum of either PMAX or 100*RI0/RI1, max(PMIN,min(PMAX,100*NI0/NI1)) is a function that returns the maximum of either (i) PMIN or (ii) the function that returns the minimum of either PMAX or 100*NI0/NI1, max(PMIN,min(PMAX,100*VB60/VB61)) is a function that returns the maximum of either (i) PMIN or (ii) the function that returns the minimum of either PMAX or 100*VB60/VB61, max(PMIN,min(PMAX,100*FO0/FO1)) is a function that returns the maximum of either (i) PMIN or (ii) the function that returns the minimum of either PMAX or 100*FO0/FO1, max(PMIN,min(PMAX,100*VB120/VB121)) is a function that returns the maximum of either (i) PMIN or (ii) the function that returns the minimum of either PMAX or 100*VB120/VB121, max(PMIN,min(PMAX,100*PA0/PA1)) is a function that returns the maximum of either (i) PMIN or (ii) the function that returns the minimum of either PMAX or 100*PA0/PA1, max(PMIN,min(PMAX,100*MG0/MG1)) is a function that returns the maximum of either (i) PMIN or (ii) the function that returns the minimum of either PMAX or 100*MG0/MG1, max(PMIN,min(PMAX,100*P0/P1)) is a function that returns the maximum of either (i) PMIN or (ii) the function that returns the minimum of either PMAX or 100*P0/P1, max(PMIN,min(PMAX,100*K0/K1)) is a function that returns the maximum of either (i) PMIN or (ii) the function that returns the minimum of either PMAX or 100*K0/K1, max(PMIN,min(PMAX,100*ZN0/ZN1)) is a function that returns the maximum of either (i) PMIN or (ii) the function that returns the minimum of either PMAX or 100*ZN0/ZN1, max(PMIN,min(PMAX,100*CU0/CU1)) is a function that returns the maximum of either (i) PMIN or (ii) the function that returns the minimum of either PMAX or 100*CU0/CU1, max(PMIN,min(PMAX,100*MN0/MN1)) is a function that returns the maximum of either (i) PMIN or (ii) the function that returns the minimum of either PMAX or 100*MN0/MN1, max(PMIN,min(PMAX,100*SE0/SE1)) is a function that returns the maximum of either (i) PMIN or (ii) the function that returns the minimum of either PMAX or 100*SE0/SE1, max(PMIN,min(PMAX,100*SF0/SF1)) is a function that returns the maximum of either (i) PMIN or (ii) the function that returns the minimum of either PMAX or 100*SF0/SF1, max(PMIN,min(PMAX,100*CH0/CH1)) is a function that returns the maximum of either (i) PMIN or (ii) the function that returns the minimum of either PMAX or 100*CH0/CH1, max(PMIN,min(PMAX,100*NA0/NA1)) is a function that returns the maximum of either (i) PMIN or (ii) the function that returns the minimum of either PMAX or 100*NA0/NA1, max(PMIN,min(PMAX,100*SA0/SA1)) is a function that returns the maximum of either (i) PMIN or (ii) the function that returns the minimum of either PMAX or 100*SA0/SA1, max(RMIN,min(RMAX,C00+C01*(ln(max(PMIN,min (PMAX,100*DF0/DF1)))−ln(PAVG))+C02*(ln(max (PMIN,min(PMAX,100*PR0/PR1)))−ln(PAVG))+ C03*(ln(max(PMIN,min(PMAX,100*VA0/VA1)))−ln (PAVG))+C04*(ln(max(PMIN,min(PMAX,100*VC0/ VC1)))−ln(PAVG))+C05*(ln(max(PMIN,min(PMAX, 100*CA0/CA1)))−ln(PAVG))+C06*(ln(max(PMIN, min(PMAX,100*FE0/FE1)))−ln(PAVG))+C07*(ln (max(PMIN,min(PMAX,100*VD0/VD1)))−ln (PAVG))+C08*(ln(max(PMIN,min(PMAX,100*VE0/ VE1)))−ln(PAVG))+C09*(ln(max(PMIN,min(PMAX, 100*VK0/VK1)))−ln(PAVG))+C10*(ln(max(PMIN, min(PMAX,100*TH0/TH1)))−ln(PAVG))+C11*(ln (max(PMIN,min(PMAX,100*RI0/RI1)))−ln(PAVG)+ C12*(ln(max(PMIN,min(PMAX,100*NI0/NI1)))−ln (PAVG))+C13*(ln(max(PMIN,min(PMAX, 100*VB60/VB61)))−ln(PAVG))+C14*(ln(max(PMIN, min(PMAX,100*FO0/FO1)))−ln(PAVG))+C15*(ln (max(PMIN,min(PMAX,100*VB120/VB121)))−ln (PAVG))+C16*(ln(max(PMIN,min(PMAX,100*PA0/ PA1)))−ln(PAVG))+C17*(ln(max(PMIN,min(PMAX, 100*MG0/MG1)))−ln(PAVG))+C18*(ln(max(PMIN, min(PMAX,100*P0/P1)))−ln(PAVG))+C19*(ln(max (PMIN,min(PMAX,100*K0/K1)))−ln(PAVG))+C20* (ln(max(PMIN,min(PMAX,100*ZN0/ZN1)))−ln (PAVG))+C21*(ln(max(PMIN,min(PMAX,100*CU0/ CU1)))−ln(PAVG))+C22*(ln(max(PMIN,min(PMAX, 100*MN0/MN1)))−ln(PAVG))+C23*(ln(max(PMIN, min(PMAX,100*SE0/SE1)))−ln(PAVG))+C24*(ln (max(PMIN,min(PMAX,100*SF0/SF1)))−ln (PAVG))+C25*(ln(max(PMIN,min(PMAX,100*CH0/ CH1)))−ln(PAVG))+C26*(ln(max(PMIN,min(PMAX, 100*NA0/NA1)))−ln(PAVG))+C27*(ln(max(PMIN, min(PMAX,100*SA0/SA1)))−ln(PAVG)))) is a function that returns the maximum of either (i) RMIN or (ii) the function that returns the minimum of either RMAX or the quantity C00+C01*(ln(max(PMIN,min (PMAX,100*DF0/DF1)))−ln(PAVG))+C02*(ln(max (PMIN,min(PMAX,100*PR0/PR1)))−ln(PAVG))+ C03*(ln(max(PMIN,min(PMAX,100*VA0/VA1)))−ln (PAVG))+C04*(ln(max(PMIN,min(PMAX,100*VC0/ VC1)))−ln(PAVG))+C05*(ln(max(PMIN,min(PMAX, 100*CA0/CA1)))−ln(PAVG))+C06*(ln(max(PMIN, min(PMAX,100*FE0/FE1)))−ln(PAVG))+C07*(ln (max(PMIN,min(PMAX,100*VD0/VD1)))−ln (PAVG))+C08*(ln(max(PMIN,min(PMAX,100*VE0/ VE1)))−ln(PAVG))+C09*(ln(max(PMIN,min(PMAX, 100*VK0/VK1)))−ln(PAVG))+C10*(ln(max(PMIN, min(PMAX,100*TH0/TH1)))−ln(PAVG))+C11*(ln (max(PMIN,min(PMAX,100*RI0/RI1)))−ln(PAVG))+ C12*(ln(max(PMIN,min(PMAX,100*NI0/NI1)))−ln (PAVG))+C13*(ln(max(PMIN,min(PMAX, 100*VB60/VB61)))−ln(PAVG))+C14*(ln(max(PMIN, min(PMAX,100*FO0/FO1)))−ln(PAVG))+C15*(ln (max(PMIN,min(PMAX,100*VB120/VB121)))−ln (PAVG))+C16*(ln(max(PMIN,min(PMAX,100*PA0/ PA1)))−ln(PAVG))+C17*(ln(max(PMIN,min(PMAX, 100*MG0/MG1)))−ln(PAVG))+C18*(ln(max(PMIN, min(PMAX,100*P0/P1)))−ln(PAVG))+C19*(ln(max (PMIN,min(PMAX,100*K0/K1)))−ln(PAVG))+C20* (ln(max(PMIN,min(PMAX,100*ZN0/ZN1)))−ln (PAVG))+C21*(ln(max(PMIN,min(PMAX,100*CU0/ CU1)))−ln(PAVG))+C22*(ln(max(PMIN,min(PMAX, 100*MN0/MN1)))−ln(PAVG))+C23*(ln(max(PMIN, min(PMAX,100*SE0/SE1)))−ln(PAVG))+C24*(ln (max(PMIN,min(PMAX,100*SF0/SF1)))−ln (PAVG))+C25*(ln(max(PMIN,min(PMAX,100*CH0/ CH1)))−ln(PAVG))+C26*(ln(max(PMIN,min(PMAX, 100*NA0/NA1)))−ln(PAVG))+C27*(ln(max(PMIN, min(PMAX,100*SA0/SA1)))−ln(PAVG))

DF0 is the amount of Dietary Fiber present in a serving,
DF1 is the amount of Dietary Fiber specified as the Daily Value by the US FDA;
PR0 is the amount of Protein present in a serving;
PR1 is the amount of Protein specified as the Daily Value by the US FDA;
VA0 is the amount of Vitamin A present in a serving;
VA1 is the amount of Vitamin A specified as the Daily Value by the US FDA;
VC0 is the amount of Vitamin C present in a serving;
VC1 is the amount of Vitamin C specified as the Daily Value by the US FDA;
CA0 is the amount of Calcium present in a serving;
CA1 is the amount of Calcium specified as the Daily Value by the US FDA;
FE0 is the amount of Iron present in a serving;
FE1 is the amount of Iron specified as the Daily Value by the US FDA;
VD0 is the amount of Vitamin D present in a serving;
VD1 is the amount of Vitamin D specified as the Daily Value by the US FDA;
VE0 is the amount of Vitamin E present in a serving;
VE1 is the amount of Vitamin E specified as the Daily Value by the US FDA;
VK0 is the amount of Vitamin K present in a serving;
VK1 is the amount of Vitamin K specified as the Daily Value by the US FDA;
TH0 is the amount of Thiamin present in a serving;
TH1 is the amount of Thiamin specified as the Daily Value by the US FDA;
RI0 is the amount of Riboflavin present in a serving;
RI1 is the amount of Riboflavin specified as the Daily Value by the US FDA;
NI0 is the amount of Niacin present in a serving;
NI1 is the amount of Niacin specified as the Daily Value by the US FDA;
VB60 is the amount of Vitamin B6 present in a serving;
VB61 is the amount of Vitamin B6 specified as the Daily Value by the US FDA;
FO0 is the amount of Folate present in a serving;
FO1 is the amount of Folate specified as the Daily Value by the US FDA;
VB120 is the amount of Vitamin B12 present in a serving;
VB121 is the amount of Vitamin B12 specified as the Daily Value by the US FDA;
PA0 is the amount of Pantothenic Acid present in a serving;
PA1 is the amount of Pantothenic Acid specified as the Daily Value by the US FDA;
MG0 is the amount of Magnesium present in a serving;
MG1 is the amount of Magnesium specified as the Daily Value by the US FDA;
P0 is the amount of Phosphorus present in a serving;
P1 is the amount of Phosphorus specified as the Daily Value by the US FDA;
K0 is the amount of Potassium present in a serving;

K1 is the amount of Potassium specified as the Daily Value by the US FDA;
ZN0 is the amount of Zinc present in a serving;
ZN1 is the amount of Zinc specified as the Daily Value by the US FDA;
CU0 is the amount of Copper present in a serving;
CU1 is the amount of Copper specified as the Daily Value by the US FDA;
MN0 is the amount of Manganese present in a serving;
MN1 is the amount of Manganese specified as the Daily Value by the US FDA;
SE0 is the amount of Selenium present in a serving;
SE1 is the amount of Selenium specified as the Daily Value by the US FDA;
SF0 is the amount of Saturated Fat present in a serving;
SF1 is the amount of Saturated Fat specified as the Daily Value by the US FDA;
CH0 is the amount of Cholesterol present in a serving;
CH1 is the amount of Cholesterol specified as the Daily Value by the US FDA;
NA0 is the amount of Sodium present in a serving;
NA1 is the amount of Sodium specified as the Daily Value by the US FDA;
SA0 is the number of Calories in a serving from sugars (as reported on Nutrition Facts labels) and alcohol; and
SA1 is the total number of Calories in a serving;
wherein:
RMIN, RMAX, PMIN, PMAX, PAVG, and C00 are constants,
C01 thru C27 are coefficients that weight the effects of the individual nutrients on the NDR; and
wherein these constants and coefficients have the following approximate values:
C00=3.0
C01=0.238
C02=0.238
C03=0.238
C04=0.238
C05=0.238
C06=0.238
C07=0.0238
C08=0.0238
C09=0.0238
C10=0.0238
C11=0.0238
C12=0.0238
C13=0.0238
C14=0.0238
C15=0.0238
C16=0.0238
C17=0.0238
C18=0.0238
C19=0.0238
C20=0.0238
C21=0.0238
C22=0.0238
C23=0.0238
C24=−0.238
C25=−0.238
C26=−0.238
C27=−0.238; and
(b) output means for providing a guideline to a user, said guideline including said first and second factors to enable food selection in accordance with at least one dietary goal.

10. A computer program product comprising a computer usable physical medium storing a computer executable program to:
(a) compute a first factor that represents an estimate of the satiating effect of a food according to the relationship:

$$FF = \max(FFMIN, \min(FFMAX, C00$$
$$+ C01 * \max(CALMIN, CAL)^{E01}$$
$$+ C02 * \min(PRMAX, PR)^{E02}$$
$$+ C03 * \min(DFMAX, DF)^{E03}$$
$$+ C04 * \min(TFMAX, TF)^{E04}))$$

where:
FF refers to "fullness factor"
max(CALMIN,CAL) is a function that returns the maximum of either (CALMIN or CAL,
min(PRMAX,PR) is a function that returns the minimum of either PRMAX or PR,
min(DFMAX,DF) is a function that returns the minimum of either DFMAX or DF,
min(TFMAX,TF) is a function that returns the minimum of either TFMAX or TF,
max(FFMIN,min(FFMAX,C00+C01*max(CALMIN, CAL)^E01+C02*min(PRMAX,PR)^E02+C03*min (DFMAX,DF)^E03+C04*min(TFMAX,TF)^E04)) is a function that returns the maximum of either (i) FFMIN or (ii) the function that returns the minimum of either FFMAX or the quantity C00+C01*max(CALMIN, CAL)^E01+C02*min(PRMAX,PR)^E02+C03*min (DFMAX,DF)^E03+C04*min(TFMAX,TF)^E04
CAL is total Calories per 100 gram portion of the food,
PR is grams of Protein per 100 g,
DF is grams Dietary Fiber per 100 g, and
TF is grams total Fat per 100 g;
FFMIN, FFMAX, CALMIN, PRMAX, DFMAX, TFMAX, and C00 are constants, C01 through C04 are coefficients, and E01 through E04 are exponential powers having the approximate following values:
FFMIN=0.5
FFMAX=5.0
CALMIN=30
PRMAX=30
DFMAX=12
TFMAX=50
C00=37/60
C01=2500/60
C02=3/60
C03=1/1620
C04=−1/138,000
E01=−0.7
E02=1.0
E03=3.0
E04=3.0; and
(b) compute a second factor that represents the nutritional benefit of said food according to the relationship:

$$NDR = \max(RMIN, \min(RMAX, C00$$
$$+ C01 * (\ln(\max(PMIN, \min(PMAX, 100*DF0/DF1))) - \ln(PAVG))$$
$$+ C02 * (\ln(\max(PMIN, \min(PMAX, 100*PR0/PR1))) - \ln(PAVG))$$
$$+ C03 * (\ln(\max(PMIN, \min(PMAX, 100*VA0/VA1))) - \ln(PAVG))$$

$+C04*(\ln(\max(PMIN,\min(PMAX,100*VC0/VC1)))-\ln(PAVG))$ $+C05*(\ln(\max(PMIN,\min(PMAX,100*CA0/CA1)))-\ln(PAVG))$ $+C06*(\ln(\max(PMIN,\min(PMAX,100*FE0/FE1)))-\ln(PAVG))$ $+C07*(\ln(\max(PMIN,\min(PMAX,100*VD0/VD1)))-\ln(PAVG))$ $+C08*(\ln(\max(PMIN,\min(PMAX,100*VE0/VE1)))-\ln(PAVG))$ $+C09*(\ln(\max(PMIN,\min(PMAX,100*VK0/VK1)))-\ln(PAVG))$ $+C10*(\ln(\max(PMIN,\min(PMAX,100*TH0/TH1)))-\ln(PAVG))$ $+C11*(\ln(\max(PMIN,\min(PMAX,100*RI0/RI1)))-\ln(PAVG))$ $+C12*(\ln(\max(PMIN,\min(PMAX,100*NI0/NI1)))-\ln(PAVG))$ $+C13*(\ln(\max(PMIN,\min(PMAX,100*VB60/VB61)))-\ln(PAVG))$ $+C14*(\ln(\max(PMIN,\min(PMAX,100*FO0/FO1)))-\ln(PAVG))$ $+C15*(\ln(\max(PMIN,\min(PMAX,100*VB120/VB121)))-\ln(PAVG))$ $+C16*(\ln(\max(PMIN,\min(PMAX,100*PA0/PA1)))-\ln(PAVG))$ $+C17*(\ln(\max(PMIN,\min(PMAX,100*MG0/MG1)))-\ln(PAVG))$ $+C18*(\ln(\max(PMIN,\min(PMAX,100*P0/P1)))-\ln(PAVG))$ $+C19*(\ln(\max(PMIN,\min(PMAX,100*K0/K1)))-\ln(PAVG))$ $+C20*(\ln(\max(PMIN,\min(PMAX,100*ZN0/ZN1)))-\ln(PAVG))$ $+C21*(\ln(\max(PMIN,\min(PMAX,100*CU0/CU1)))-\ln(PAVG))$ $+C22*(\ln(\max(PMIN,\min(PMAX,100*MN0/MN1)))-\ln(PAVG))$ $+C23*(\ln(\max(PMIN,\min(PMAX,100*SE0/SE1)))-\ln(PAVG))$ $+C24*(\ln(\max(PMIN,\min(PMAX,100*SF0/SF1)))-\ln(PAVG))$ $+C25*(\ln(\max(PMIN,\min(PMAX,100*CH0/CH1)))-\ln(PAVG))$ $+C26*(\ln(\max(PMIN,\min(PMAX,100*NA0/NA1)))-\ln(PAVG))$ $+C27*(\ln(\max(PMIN,\min(PMAX,100*SA0/SA1)))-\ln(PAVG)))$ where:
NDR refers to "nutrient density"
ln is the natural (base e) logarithm, max(PMIN,min(PMAX,100*DF0/DF1) is a function that returns the maximum of either (i) PMIN or (ii) the function that returns the minimum of either PMAX or 100*DF0/DF1, max(PMIN,min(PMAX,100*PR0/PR1)) is a function that returns the maximum of either (i) PMIN or (ii) the function that returns the minimum of either PMAX or 100*PR0/PR1, max(PMIN,min(PMAX,100*VA0/VA1)) is a function that returns the maximum of either (i) PMIN or (ii) the function that returns the minimum of either PMAX or 100*VA0/VA1, max(PMIN min(PMAX,100*VC0/VC1)) is a function that returns the maximum of either (i) PMIN or (ii) the function that returns the minimum of either PMAX or 100*VC0/VC1, max(PMIN,min(PMAX,100*CA0/CA 1)) is a function that returns the maximum of either (i) PMIN or (ii) the function that returns the minimum of either PMAX or 100*CA0/CA1, max(PMIN,min(PMAX,100*FE0/FE1)) is a function that returns the maximum of either (i) PMIN or (ii) the function that returns the minimum of either PMAX or 100*FE0/FE1, max(PMIN,min(PMAX,100*VD0/VD1)) is a function that returns the maximum of either (i) PMIN or (ii) the function that returns the minimum of either PMAX or 100*VD0/VD1, max(PMIN,min(PMAX,100*VE0V/E1)) is a function that returns the maximum of either (i) PMIN or (ii) the function that returns the minimum of either PMAX or 100*VE0/VE1, max(PMIN,min(PMAX,100*VK0/VK1)) is a function that returns the maximum of either (i) PMIN or (ii) the function that returns the minimum of either PMAX or 100*VK0/VK1, max(PMIN,min(PMAX,100*TH0/TH1)) is a function that returns the maximum of either (i) PMIN or (ii) the function that returns the minimum of either PMAX or 100*TH0/TH1, max(PMIN,min(PMAX,100*RI0/RI1)) is a function that returns the maximum of either (i) PMIN or (ii) the function that returns the minimum of either PMAX or 100*RI0/RI1, max(PMIN,min(PMAX,100*NI0/NI1)) is a function that returns the maximum of either (i) PMIN or (ii) the function that returns the minimum of either PMAX or 100*NI0/NI1, max(PMIN,min(PMAX,100*VB60/VB61)) is a function that returns the maximum of either (i) PMIN or (ii) the function that returns the minimum of either PMAX or 100*VB60/VB61, max(PMIN,min(PMAX,100*FO0/FO1)) is a function that returns the maximum of either (i) PMIN or (ii) the function that returns the minimum of either PMAX or 100*FO0/FO1, max(PMIN,min(PMAX,100*VB120/VB121)) is a function that returns the maximum of either (i) PMIN or (ii) the function that returns the minimum of either PMAX or 100*VB120/VB121, max(PMIN,min(PMAX,100*PA0/PA1)) is a function that returns the maximum of either (i) PMIN or (ii) the function that returns the minimum of either PMAX or 100*PA0/PA1, max(PMIN,min(PMAX,100*MG0/MG1)) is a function that returns the maximum of either (i) PMIN or (ii) the function that returns the minimum of either PMAX or 100*MG0/MG1, max(PMIN,min(PMAX,100*P0/P1)) is a function that returns the maximum of either (i) PMIN or (ii) the function that returns the minimum of either PMAX or 100*P0/P1, max(PMIN,min(PMAX,100*K0/K1)) is a function that returns the maximum of either (i) PMIN or (ii) the function that returns the minimum of either PMAX or 100*K0/K1, max(PMIN,min(PMAX,100*ZN0/ZN1)) is a function that returns the maximum of either (i) PMIN or (ii) the function that returns the minimum of either PMAX or 100*ZN0/ZN1, max(PMIN,min(PMAX,100*CU0/CU1)) is a function that returns the maximum of either (i) PMIN or (ii) the function that returns the minimum of either PMAX or 100*CU0/CU1, max(PMIN,min(PMAX,100*MN0/MN1)) is a function that returns the maximum of either (i) PMIN or (ii) the function that returns the minimum of either PMAX or 100*MN0/MN1, max(PMIN,min(PMAX,100*SE0/SE1)) is a function that returns the maximum of either (i) PMIN or (ii) the function that returns the minimum of either PMAX or 100*SE0/SE1, max(PMIN,min(PMAX,100*SF0/SF1)) is a function that returns the maximum of either (i) PMIN or (ii) the function that returns the minimum of either PMAX or 100*SF0/SF1, max(PMIN,min(PMAX,100*CH0/CH1)) is a function that returns the maximum of either (i) PMIN or (ii) the function that returns the minimum of either PMAX or 100*CH0/CH1, max(PMIN,min(PMAX,100*NA0/NA1)) is a function that returns the maximum of either (i) PMIN or (ii) the function that returns the minimum of either PMAX or 100*NA0/NA1, max(PMIN,min(PMAX,100*SA0/SA1)) is a function that returns the maximum of either (i) PMIN or (ii) the function that returns the minimum of either PMAX or 100*SA0/SA1, max(RMIN,min(RMAX,C00+C01*(ln(max(PMIN,min(PMAX,100*DF0/DF1)))−ln(PAVG))+C02*(ln(max(PMIN,min(PMAX,100*PR0/PR1)))−ln(PAVG))+C03*(ln(max(PMIN,min(PMAX,100*VA0/VA1)))−ln(PAVG))+C04*(ln(max(PMIN,min(PMAX,100*VC0/VC1)))−ln(PAVG))+C05*(ln(max(PMIN,min(PMAX,100*CA0/CA1)))−ln(PAVG))+C06*(ln(max(PMIN,min(PMAX,100*FE0/FE1)))−ln(PAVG))+C07*(ln(max(PMIN,min(PMAX,100*VD0/VD1)))−ln(PAVG))+C08*(ln(max(PMIN,min(PMAX,100*VE0/VE1)))−ln(PAVG))+C09*(ln(max(PMIN,min(PMAX,100*VK0/VK1)))−ln(PAVG)+C10*(ln(max(PMIN,min(PMAX,100*TH0/TH1)))−ln(PAVG))+C11*(ln(max(PMIN,min(PMAX,100*RI0/RI1)))−ln(PAVG)+C12*(ln(max(PMIN,min(PMAX,100*NI0/NI1)))−ln(PAVG))+C13*(ln(max(PMIN,min(PMAX,100*VB60/VB61)))−ln(PAVG))+C14*(ln(max(PMIN,min(PMAX,100*FO0/FO1)))−ln(PAVG))+C15*(ln(max(PMIN,min(PMAX,100*VB120/VB121)))−ln(PAVG))+C16*(ln(max(PMIN,min(PMAX,100*PA0/PA1)))−ln(PAVG))+C17*(ln(max(PMIN,min(PMAX,100*MG0/MG1)))−ln(PAVG))+C18*(ln(max(PMIN,min(PMAX,100*P0/P1)))−ln(PAVG))+C19*(ln(max(PMIN,min(PMAX,100*K0/K1)))−ln(PAVG))+C20*(ln(max(PMIN,min(PMAX,100*ZN0/ZN1)))−ln(PAVG))+C21*(ln(max(PMIN,min(PMAX,100*CU0/CU1)))−ln(PAVG))+C22*(ln(max(PMIN,min(PMAX,100*MN0/MN1)))−ln(PAVG))+C23*(ln(max(PMIN,min(PMAX,100*SE0/SE1)))−ln(PAVG))+C24*(ln(max(PMIN,min(PMAX,100*SF0/SF1)))−ln(PAVG))+C25*(ln(max(PMIN,min(PMAX,100*CH0/CH1)))−ln(PAVG))+C26*(ln(max(PMIN,min(PMAX,100*NA0/NA1)))−ln(PAVG))+C27*(ln(max(PMIN,min(PMAX,100*SA0/SA1)))−ln(PAVG)))) is a function that returns the maximum of either (i) RMIN or (ii) the function that returns the minimum of either RMAX or the quantity C00+C01*(ln(max(PMIN,min(PMAX,100*DF0/DF1)))−ln(PAVG))+C02*(ln(max(PMIN,min(PMAX,100*PR0/PR1)))−ln(PAVG))+C03*(ln(max(PMIN,min(PMAX,100*VA0/VA1)))−ln(PAVG))+C04*(ln(max(PMIN,min(PMAX,100*VC0/VC1)))−ln(PAVG))+C05*(ln(max(PMIN,min(PMAX,100*CA0/CA1)))−ln(PAVG))+C06*(ln(max(PMIN,min(PMAX,100*FE0/FE1)))−ln(PAVG))+C07*(ln(max(PMIN,min(PMAX,100*VD0/VD1)))−ln(PAVG))+C08*(ln(max(PMIN,min(PMAX,100*VE0/VE1)))−ln(PAVG))+C09*(ln(max(PMIN,min(PMAX,100*VK0/VK1)))−ln(PAVG)+C10*(ln(max(PMIN,min(PMAX,100*TH0/TH1)))−ln(PAVG))+C11*(ln(max(PMIN,min(PMAX,100*RI0/RI1)))−ln(PAVG))+C12*(ln(max(PMIN,min(PMAX,100*NI0/NI1)))−ln(PAVG))+C13*(ln(max(PMIN,min(PMAX,100*VB60/VB61)))−ln(PAVG))+C14*(ln(max(PMIN,min(PMAX,100*FO0/FO1)))−ln(PAVG))+C15*(ln(max(PMIN,min(PMAX,100*VB120/VB121)))−ln(PAVG))+C16*(ln(max(PMIN,min(PMAX,100*PA0/PA1)))−ln(PAVG))+C17*(ln(max(PMIN,min(PMAX,100*MG0/MG1)))−ln(PAVG))+C18*(ln(max(PMIN,min(PMAX,100*P0/P1)))−ln(PAVG))+C19*(ln(max(PMIN,min(PMAX,100*K0/K1)))−ln(PAVG))+C20*(ln(max(PMIN,min(PMAX,100*ZN0/ZN1)))−ln(PAVG))+C21*(ln(max(PMIN,min(PMAX,100*CU0/CU1)))−ln(PAVG))+C22*(ln(max(PMIN,min(PMAX,100*MN0/MN1)))−ln(PAVG))+C23*(ln(max(PMIN,min(PMAX,100*SE0/SE1)))−ln(PAVG))+C24*(ln(max(PMIN,min(PMAX,100*SF0/SF1)))−ln(PAVG))+C25*(ln(max(PMIN,min(PMAX,100*CH0/CH1)))−ln(PAVG))+C26*(ln(max(PMIN,min(PMAX,100*NA0/NA1)))−ln(PAVG))+C27*(ln(max(PMIN,min(PMAX,100*SA0/SA1)))−ln(PAVG)), DF0 is the amount of Dietary Fiber present in a serving;
DF1 is the amount of Dietary Fiber specified as the Daily Value by the US FDA;
PR0 is the amount of Protein present in a serving;
PR1 is the amount of Protein specified as the Daily Value by the US FDA;
VA0 is the amount of Vitamin A present in a serving;
VA1 is the amount of Vitamin A specified as the Daily Value by the US FDA;
VC0 is the amount of Vitamin C present in a serving;
VC1 is the amount of Vitamin C specified as the Daily Value by the US FDA;
CA0 is the amount of Calcium present in a serving;
CA1 is the amount of Calcium specified as the Daily Value by the US FDA;
FE0 is the amount of Iron present in a serving;
FE1 is the amount of Iron specified as the Daily Value by the US FDA;
VD0 is the amount of Vitamin D present in a serving;

VD1 is the amount of Vitamin D specified as the Daily Value by the US FDA;
VE0 is the amount of Vitamin E present in a serving;
VE1 is the amount of Vitamin E specified as the Daily Value by the US FDA;
VK0 is the amount of Vitamin K present in a serving;
VK1 is the amount of Vitamin K specified as the Daily Value by the US FDA;
TH0 is the amount of Thiamin present in a serving;
TH1 is the amount of Thiamin specified as the Daily Value by the US FDA;
RI0 is the amount of Riboflavin present in a serving;
RI1 is the amount of Riboflavin specified as the Daily Value by the US FDA;
NI0 is the amount of Niacin present in a serving;
NI1 is the amount of Niacin specified as the Daily Value by the US FDA;
VB60 is the amount of Vitamin B6 present in a serving;
VB61 is the amount of Vitamin B6 specified as the Daily Value by the US FDA;
FO0 is the amount of Folate present in a serving;
FO1 is the amount of Folate specified as the Daily Value by the US FDA;
VB120 is the amount of Vitamin B12 present in a serving;
VB121 is the amount of Vitamin B12 specified as the Daily Value by the US FDA;
PA0 is the amount of Pantothenic Acid present in a serving;
PA1 is the amount of Pantothenic Acid specified as the Daily Value by the US FDA;
MG0 is the amount of Magnesium present in a serving;
MG1 is the amount of Magnesium specified as the Daily Value by the US FDA;
P0 is the amount of Phosphorus present in a serving;
P1 is the amount of Phosphorus specified as the Daily Value by the US FDA;
K0 is the amount of Potassium present in a serving;
K1 is the amount of Potassium specified as the Daily Value by the US FDA;
ZN0 is the amount of Zinc present in a serving;
ZN1 is the amount of Zinc specified as the Daily Value by the US FDA;
CU0 is the amount of Copper present in a serving;
CU1 is the amount of Copper specified as the Daily Value by the US FDA;
MN0 is the amount of Manganese present in a serving;
MN1 is the amount of Manganese specified as the Daily Value by the US FDA;
SE0 is the amount of Selenium present in a serving;
SE1 is the amount of Selenium specified as the Daily Value by the US FDA;
SF0 is the amount of Saturated Fat present in a serving;
SF1 is the amount of Saturated Fat specified as the Daily Value by the US FDA;
CH0 is the amount of Cholesterol present in a serving;
CH1 is the amount of Cholesterol specified as the Daily Value by the US FDA;
NA0 is the amount of Sodium present in a serving;
NA1 is the amount of Sodium specified as the Daily Value by the US FDA;
SA0 is the number of Calories in a serving from sugars (as reported on Nutrition Facts labels) and alcohol; and
SA1 is the total number of Calories in a serving;
wherein:
RMIN, RMAX, PMIN, PMAX, PAVG, and C00 are constants,
C01 thru C27 are coefficients that weight the effects of the individual nutrients on the NDR; and wherein these constants and coefficients have the following approximate values:
RMIN=0.0
RMAX=5.0
PMIN=2.5
PMAX=40
PAVG=10
C00=3.0
C01=0.238
C02=0.238
C03=0.238
C04=0.238
C05=0.238
C06=0.238
C07=0.0238
C08=0.0238
C09=0.0238
C10=0.0238
C11=0.0238
C12=0.0238
C13=0.0238
C14=0.0238
C15=0.0238
C16=0.0238
C17=0.0238
C18=1.0238
C19=0.0238
C20=0.0238
C21=0.0238
C22=0.238
C23=0.0238
C24=−0.238
C25=−0.238
C26=−0.238
C27=−0.238; and (c) provide a guideline to a user including said first and second factors to enable food selection in accordance with at least one dietary goal.

11. A method of rating food, comprising the steps of:
(a) calculating a first factor that represents an estimate of the satiating effect of a food;
(b) calculating a second factor that represents the nutritional benefit of said food;
(c) combining said first and second factors to yield a single indicator of suitability of said food for at least one dietary goal, said single indicator being representative of a relationship between (i) said first and second factors and (ii) satiety and nutritional values which represent fulfillment of said at least one dietary goal; and
(d) providing to a user a guideline including said single indicator to enable food selection in accordance with said at least one dietary goal;
wherein at least one of steps (a), (b) and (c) is effected using a suitably programmed computer.

12. The method of claim 11, wherein said step of providing to a user a guideline includes providing a graphical representation including regions associated with different ones of said at least one dietary goal.

13. The method of claim 11, wherein said guideline includes regions based on nutritional characteristics for preselected nutritional goals.

14. The method of claim 11, further comprising the step of plotting said first and second factors as a first graphical coordinate pair and said satiety and nutritional values which represent fulfillment of said at least one dietary goal as a second graphical coordinate pair, and wherein said relationship describes a difference between said first graphical coordinate pair and said second graphical coordinate pair.

15. The method of claim 11 wherein said step of calculating a first factor is based on the calorie, protein, dietary fiber and total fat content of said food and said step of calculating a second factor is based on content of nutrients, said content of nutrients including said protein content, selected vitamin and selected mineral content, and Daily Values for said nutrients.

16. The method of claim 15, wherein said Daily Values are specified by the United States Food and Drug Administration.

17. A food rating system, comprising:
a data processor adapted to (i) calculate a first factor that represents an estimate of the satiating effect of a food and a second factor that represents the nutritional benefit of said food and (ii) combine said first and second factors into a single indicator representative of a relationship between (a) said first and second factors and (b) satiety and nutritional values which represent fulfillment of at least one dietary goal; and output means for providing a guideline to a user, said guideline including said single indicator to enable food selection in accordance with said at least one dietary goal.

18. The system of claim 17, wherein said first factor is a numerical expression of caloric density of said food.

19. The system of claim 17, wherein said second factor is a numerical expression of nutrient density of said food.

20. The system of claim 17, wherein said data processor is adapted to plot said first and second factors as a first graphical coordinate pair and said satiety and nutritional values which represent fulfillment of said at least one dietary goal as a second graphical coordinate pair, and wherein said relationship describes a difference between said first graphical coordinate pair and said second graphical coordinate pair.

21. The system of claim 17, wherein said guideline is divided into regions based on nutritional characteristics of said food.

22. The system of claim 17, wherein said guideline is a graphical representation including regions associated with different ones of said at least one dietary goal.

23. The system of claim 22, wherein said single indicator corresponds to one of said regions.

24. The system of claim 17, wherein said first factor is calculated based on calorie, protein, dietary fiber and total fat content of said food; and said second factor is calculated based on content of nutrients, said content of nutrients including said dietary fiber and said protein content, and selected vitamin and selected mineral content, and Daily Values for said nutrients.

25. The system of claim 24, wherein said Daily Values are specified by the United States Food and Drug Administration.

26. A computer program product comprising a computer usable physical medium storing a computer executable program to:
(a) compute a first factor that represents an estimate of the satiating effect of a food;
(b) compute a second factor that represents the nutritional benefit of said food;
(c) combine said first and second factors into a single indicator of suitability of said food for at least one dietary goal, said single indicator being representative of a relationship between (i) said first and second factors and (ii) satiety and nutritional values which represent fulfillment of said at least one dietary goal; and
(d) provide a guideline including said single indicator to a user to enable food selection in accordance with said at least one dietary goal.

27. The computer program product of claim 26, wherein said first factor is a numerical expression of caloric density of said food.

28. The computer program product of claim 26, wherein said second factor is a numerical expression of nutrient density of said food.

29. The computer program product of claim 26, wherein said guideline is a graphical representation including regions associated with different ones of said at least one dietary goal.

30. The computer program product of claim 29, wherein said single indicator corresponds to one of said regions.

31. The computer program product of claim 26, wherein said first and second factors are plotted as a first graphical coordinate pair and said satiety and nutritional values which represent fulfillment of said at least one dietary goal are plotted as a second graphical coordinate pair, and wherein said relationship describes a difference between said first graphical coordinate pair and said second graphical coordinate pair.

32. The computer program product of claim 26, wherein said guideline is divided into regions based on nutritional characteristics of said food.

33. The computer program product of claim 26, wherein said first factor is computed based on calorie, protein, dietary fiber and total fat content of said food; and said second factor is computed based on content of nutrients, said content of nutrients including said dietary fiber and said protein content, and selected vitamin and selected mineral content, and Daily Values for said nutrients.

34. The computer program product of claim 33, wherein said Daily Values are specified by the United States Food and Drug Administration.

* * * * *